United States Patent [19]

Shen et al.

[11] Patent Number: 5,530,141
[45] Date of Patent: Jun. 25, 1996

[54] 2,4-DIARYL-1,3-DITHIOLANES; 2,4-DIARYL-1,3-DIOXOLANES; 2,4-DIARYL-1,3-OXATHIOLANES; AND 2,5-DIARYL-1,3-OXATHIOLANES FOR THE TREATMENT OF DISORDERS MEDIATED BY PLATELET ACTIVATING FACTOR OR PRODUCTS OF 5-LIPOXYGENASE

[75] Inventors: T. Y. Shen, Charlottesville, Va.; David M. Goldstein, Pittsburgh, Pa.

[73] Assignee: Center for Innovative Technology, Herndon, Va.

[21] Appl. No.: 944,845

[22] Filed: Sep. 14, 1992

[30] Foreign Application Priority Data

Mar. 4, 1992 [WO] WIPO ............... PCT/US92/01830

[51] Int. Cl.$^6$ ............... C07D 339/02
[52] U.S. Cl. ............... 549/39; 549/30; 549/35; 549/36; 549/37; 549/38; 544/145; 546/206
[58] Field of Search ............... 549/39, 30, 35, 549/36, 37, 38; 546/200; 544/145

[56] References Cited

U.S. PATENT DOCUMENTS

| | | |
|---|---|---|
| 4,539,332 | 9/1985 | Biftu et al. . |
| 4,757,084 | 7/1988 | Biftu et al. . |
| 4,910,206 | 3/1990 | Houlihan . |
| 4,916,145 | 4/1990 | Tilley et al. . |
| 4,959,361 | 9/1990 | Walser . |
| 4,987,132 | 1/1991 | Mase et al. . |
| 4,992,428 | 2/1991 | Houlihan et al. . |
| 4,996,203 | 2/1991 | Biftu et al. . |
| 5,001,123 | 3/1991 | Biftu et al. . |

FOREIGN PATENT DOCUMENTS

| | | |
|---|---|---|
| 0252823A1 | 1/1988 | European Pat. Off. . |
| 0319947A2 | 6/1989 | European Pat. Off. . |
| 0338993A1 | 10/1989 | European Pat. Off. . |
| 0365089A2 | 4/1990 | European Pat. Off. . |
| 0367110A1 | 5/1990 | European Pat. Off. . |
| 0388309A2 | 9/1990 | European Pat. Off. . |
| 0402150A1 | 12/1990 | European Pat. Off. . |
| 0402151A1 | 12/1990 | European Pat. Off. . |
| 0416609A2 | 3/1991 | European Pat. Off. . |
| 3701344A1 | 7/1987 | Germany . |
| 3724164A1 | 1/1988 | Germany . |
| 3724031A1 | 1/1988 | Germany . |
| 3936828A1 | 5/1990 | Germany . |
| 4006471A1 | 9/1990 | Germany . |
| 2233974 | 1/1991 | United Kingdom . |
| WO90/12015 | 10/1990 | WIPO . |
| WO92/15294 | 9/1992 | WIPO . |

OTHER PUBLICATIONS

Biftu, T. et al., "Confirmation and Activity of Tetrahydrofuran Lignans and Analogues as Specific Platelet Activating Factor Antagonists," *J. Med. Chem.* vol. 29, No. 10 (1986) pp. 1917–1921.

Corey, E. J. et al., "Dual Binding Modes to the Receptor for Platelet Activating Factor (PAF) of Anti–PAF Trans–2, 5–Diarylfurans," *Tetrahedron Letters*, vol. 29, No. 24 (1988) pp. 2899–2902.

Ponpipom, M. M., et al., "(±)–Trans–2–[3–Methylsulfonyl)–4–Propoxyphenyl)–5–(3,4,5–Trimethoxyphenyl)Tetrahydrofuran (L–659,989), A Novel, Potent PAF Receptor Antagonist," *Biochemical and Biophysical Research Communications*, vol. 150, No. 3 (1988) pp. 1213–1220.

Musser, J. H., et al., "5–Lipoxygenase: Properties, Pharmacology, and the Quinolinyl(bridge)aryl and Class of Inhibitors," *J. Med. Chem.*, vol. 35, No. 14 (1992) pp. pp. 2502–2524.

Guthrie, R. W., et al., "Propenyl Carboxamide Derivatives As Antagonists of Platelet Activating Factor," *J. Med. Chem.* vol. 33 (1990) pp. 2856–2864.

Graham, D. W., et al., "1,3–Diarylcyclopentanes: A New Class of Potent PAF Receptor Antagonists," *MEDI*, 1989.

Bartroli, J. *J. Med. Chem.*, vol. 34 (1991) pp. 3328–3334.

Carlcellar, E., et al., *J. Med. Chem.*, vol. 35 (1992) pp. 676–683.

Crawley, G. C., "Methoxytetrahydropyrans, A New Series of Selective and Orally Potent 5–Lipoxygenase Inhibitors," *J. Med. Chem.*, vol. 35, No. 14 (1992) pp. 2600–2609.

Lave, D., et al., "Pyrrolo(1,2-c)Thiazole Derivatives: Potent PAF Receptor Antagonists," *Drugs of the Future*, vol. 14, No. 9 (1989) pp. 891–898.

Ogiso, A., et al., "The Structure of Futoenone, A Novel Spiro–Cyclohexedienone Derivative," *Tetrahedron Letters*, No. 16, (1968) pp. 2003–2008.

Ogiso, A., et al., "The Structure and Total Synthesis of Futoenone, a Constitute of *Piper futokadzura* SIEB, et ZUCC"., Chem. Pharm. Bull., vol. 18, No. 1, (1970) pp. 105–114.

Ponpipom, M. M., et al., "Structure–Activity Relationships of Kadsurenone Analogues," *J. Med. Chem.*, vol. 30 (1987) pp. 136–142.

(List continued on next page.)

*Primary Examiner*—José G. Dees
*Assistant Examiner*—Samuel Barts
*Attorney, Agent, or Firm*—Cheryl K. Zalesky; Kilpatrick & Cody

[57] ABSTRACT

2,4-Diaryl-1,3-dithiolanes; 2,4-diaryl-1,3-dioxolanes; 2,4-diaryl-1,3-oxathiolanes; and 2,5-diaryl-1,3-oxathiolanes are disclosed that reduce the chemotaxis and respiratory burst leading to the formation of damaging oxygen radicals of polymorphonuclear leukocytes during an inflammatory or immune response. The compounds exhibit this biological activity by acting as PAF receptor antagonists, by inhibiting the enzyme 5-lipoxygenase, or by exhibiting dual activity, i.e., by acting as both a PAF receptor antagonist and inhibitor of 5-lipoxygenase.

A method to treat disorders mediated by PAF or leukotrienes is also disclosed, that includes administering an effective amount of one or more of the above-identified compounds or a pharmaceutically acceptable salt thereof, optionally in a pharmaceutically acceptable carrier.

29 Claims, No Drawings

OTHER PUBLICATIONS

Shen, T. Y., "Characterization of a Platelet–Activating Factor Receptor Antagonist Isolated from Halifenteng (*Piper futokadsura*): Specific Inhibition of *in vivo* and *in vivo* Platelet–Activating Factor–Induced Effects," *Proc. Natl. Acad. Sci. USA*, vol. 82, (Feb. 1985) pp. 672–676.

Weber, K. H., et al., "Hetrazepines as Antagonists of Platelet Activating Factor," *Medicinal Research Reviews*, vol. 9, No. 1 (Jan.–Mar. 1989) pp. 181–218.

Feinmark, S. J., "Leukotriene $C_4$ Biosynthesis during Polymorphonuclear Leukocyte–Vascular Cell Interactions," *Methods in Enzymology*, vol. 187, pp. 559–560, 1990.

Hwang, S., "Specific Receptors of Platelet–Activating Factor, Receptor Heterogeneity, and Signal Transduction Mechanisms," *J. Lipid Mediators*, vol. 2 (1990) pp. 123–158.

McColl, S. R., "Determination of 5–Lipoxygenase Activity in Human Polymorphonuclear Leukocytes Using High–Performance Liquid Chromatography," *J. Chromatography*, vol. 378 (1986) pp. 44–449.

O'Donnell, M., et al., "Comparison of the Pulmonary Pharmacology of Lukotrienes and PAF: Effects of their Antagonists," *Therapeutic Approaches to Inflammatory Diseases* Proceedings of the Fourth International Conference of the Inflammatory Research Association, Oct. 23–27, 1988, White Haven, Pennsylvania, p. 169.

Page, C., et al., "PAF: New Antagonists New Roles in Diseases and a Major Role in Reproductive Biology," *3rd International Conference on Platelet–Activating Factor and Structurally Related Alkyl Ether Lipids,* Tokyo, Japan, May 8–12, 1989.

Shen, T. Y., et al., "The Chemical and Biological Propertie of PAF Agonists, Antagonists, and Biosynthetic Inhibitors," *Platelet–Activating Factor and Related Mediators,* Plenum Press, New York, NY, pp. 153–190, 1989.

2,4-DIARYL-1,3-DITHIOLANES; 2,4-DIARYL-1,3-DIOXOLANES; 2,4-DIARYL-1,3-OXATHIOLANES; AND 2,5-DIARYL-1,3-OXATHIOLANES FOR THE TREATMENT OF DISORDERS MEDIATED BY PLATELET ACTIVATING FACTOR OR PRODUCTS OF 5-LIPOXYGENASE

BACKGROUND OF THE INVENTION

This invention is in the area of pharmaceutical compositions and methods for the treatment of inflammatory and immune disorders, and specifically provides novel compounds that reduce the chemotaxis and respiratory burst leading to the formation of damaging oxygen radicals of polymorphonuclear leukocytes during an inflammatory or immune response. The compounds exhibit this biological activity by acting as PAF receptor antagonists, by inhibiting the enzyme 5-lipoxygenase, or by exhibiting dual activity, i.e., by acting as both a PAF receptor antagonist and inhibitor of 5-lipoxygenase.

Platelet activating factor (PAF, 1-O-alkyl-2-acetyl-sn-glycerol-3-phosphorylcholine) is a potent inflammatory phospholipid mediator with a wide variety of biological activities. PAF was initially identified as a water soluble compound released by immunoglobulin E (IgE)-sensitized rabbit basophils. It is now known that PAF is also generated and released by monocytes, macrophages, polymorphonuclear leukocytes (PMNs), eosinophils, neutrophils, natural killer lymphocytes, platelets and endothelial cells, as well as by renal and cardiac tissues under appropriate immunological and non-immunological stimulation. (Hwang, "Specific receptors of platelet-activating factor, receptor heterogeneity, and signal transduction mechanisms", *Journal of Lipid Mediators* 2, 123 (1990)). PAF causes the aggregation and degranulation of platelets at very low concentrations. The potency (active at $10^{-12}$ to $10^{-9}$M), tissue level (picomoles) and short plasma half life (2–4 minutes) of PAF are similar to those of other lipid mediators such as thromboxane $A_2$, prostaglandins, and leukotrienes.

PAF mediates biological responses by binding to specific PAF receptors found in a wide variety of cells and tissues. Structure-activity studies on PAF and its analogs indicate that the ability of PAF to bind to these receptors is highly structure specific and stereospecific. (Shen, et al., "The Chemical and Biological Properties of PAF Agonists, Antagonists, and Biosynthetic Inhibitors", *Platelet-Activating Factor and Related Lipid Mediators*, F. Synder, Ed. Plenum Press, New York, N.Y. 153 (1987)).

While PAF mediates essential biological responses, it also appears to play a role in pathological immune and inflammatory responses. Many published studies have provided evidence for the involvement of PAF in human diseases, including arthritis, acute inflammation, asthma, endotoxic shock, pain, psoriasis, ophthalmic inflammation, ischemia, gastrointestinal ulceration, myocardial infarction, inflammatory bowel diseases, and acute respiratory distress syndrome. Animal models also demonstrate that PAF is produced or increased in certain pathological states.

The involvement of PAF in pathological inflammatory and immune states has stimulated a substantial research effort to identify PAF receptor antagonists. In 1983, a phospholipid analog referred to as CV-3988 (rac-3-(N-n-octadecyl-carbamoyloxy-w-methoxypropyl-2-thiazolioethyl phosphate) was reported to have PAF receptor antagonist properties. (Terashita, et al., *Life Sciences* 32, 1975 (1983).) In other early work in this area, Shen, et al., (in *Proc. Natl. Acad. Sci. (U.S.A.)* 82, 672 (1985)), reported that kadsurenone, a neolignan derivative isolated from *Piper futokadsura* Sieb et Zucc (a Chinese herbal plant) was a potent, specific and competitive inhibitor of PAF activity at the receptor level.

Hwang, et al., disclosed in 1985 that trans-2,5-bis-(3,4,5-trimethoxyphenyl) tetrahydrofuran (L-652,731) inhibits the binding of tritiated PAF to PAF receptor sites. (Hwang, et al., "Trans-2,5-bis-(3,4,5-trimethoxyphenyl)tetrahydrofuran", *Journal of Biological Chemistry* 260, 15639 (1985).) L-652,731 was found to be orally active, and to inhibit PAF-induced rat cutaneous vascular permeability at a dosage of 30 mg/kg body weight. This compound was found to have no effect on the enzyme 5-lipoxygenase. Hwang, et al. also reported that trans-L-652,731 (wherein the aryl groups at the 2 and 5 positions are on opposite sides of the plane of the tetrahydrofuran ring) is approximately 1000 times more potent than cis-L-652,731 (wherein the 2 and 5 aryl substituents are on the same side of the plane of the tetrahydrofuran ring).

IN 1988, Hwang, et al., reported that L-659,989 (trans-2-(3-methoxy-4-propoxyphenyl-5-methylsulfonyl)-5-(3,4,5-trimethoxyphenyl)tetrahydrofuran) is an orally active, potent, competitive PAF receptor antagonist, with an equilibrium inhibition constant 10 times greater than that of trans-L-652,731. (Hwang, et al., *J. Pharmacol. Ther.* 246, 534 (1988).)

U.S. Pat. Nos. 4,996,203, 5,001,123 and 4,539,332 to Biftu, et al. and European Patent Application Nos. 89202593.3, 90306235.4, and 90306234.7 discloses that a specific class of 2,5-diaryl tetrahydrofurans are PAF receptor antagonists.

Leukotrienes, like PAF, are potent local mediators, playing a major role in inflammatory and allergic responses, including arthritis, asthma, psoriasis, and thrombotic disease. Leukotrienes are straight chain eicosanoids produced by the oxidation of arachidonic acid by lipoxygenases. Arachidonic acid is oxidized by 5-lipoxygenase to the hydroperoxide 5-hydroperoxyeicosatetraenoic acid (5-HPETE), that is converted to leukotriene $A_4$, that in turn can be converted to leukotriene $B_4$, $C_4$, or $D_4$. The slow-reacting substance of anaphylaxis is now known to be a mixture of leukotrienes $C_4$, $D_4$, and $E_4$, all of which are potent bronchoconstrictors. There has been a research effort to develop specific receptor antagonists or inhibitors of leukotriene biosynthesis, to prevent or minimize pathogenic inflammatory responses mediated by these compounds.

Leukotrienes are released simultaneously from leukocytes with PAF, possibly from a common phospholipid precursor such as 1-O-hexadecyl-2-arachidonyl-sn-glycerophosphocholine, and upon cellular activation, act synergistically with PAF in many biological models. Recently, it was reported that the tetrahydrothiophene derivative of L-652,731, trans-2,5-bis-(3,4,5-trimethoxyphenyl)tetrahydrothiophene (L-653,150), is a potent PAF antagonist and a moderate inhibitor of 5-lipoxygenase. It has been disclosed that certain 2,5-diaryl tetrahydrothiophenes are PAF antagonists and leukotriene synthesis inhibitors. (Biftu, et al., *Abstr. of 6$^{th}$ Int. Conf. on Prostaglandins and Related Compounds*, Jun. 3–6, 1986, Florence, Italy; U.S. Pat. No. 4,757,084 to Biftu) European Patent Application Nos. 90117171.0 and 901170171.0 disclose indole, benzofuran, and benzothiphene lipoxygenase inhibiting compounds.

Given the significant number of pathological immune and inflammatory responses that are mediated by PAF and leukotrienes, there remains a need to identify new compounds and compositions that exhibit PAF receptor antagonistic activity or inhibit the enzyme 5-lipoxygenase.

Therefore, it is an object of the present invention to provide compounds that reduce the chemotaxis and respiratory burst leading to the formation of damaging oxygen radicals during an inflammatory or immune response.

It is another object of the present invention to provide pharmaceutical compositions for the treatment of pathological immune or inflammatory disorders mediated by PAF or products of 5-lipoxygenase.

It is another object of the present invention to provide a method for the treatment of pathological immune or inflammatory disorders mediated by PAF or products of 5-lipoxygenase.

SUMMARY OF THE INVENTION

Organic compounds (2,4-diaryl-1,3-dithiolanes; 2,4-diaryl-1,3-dioxolanes; 2,4-diaryl-1,3-oxathiolanes; and 2,5-diaryl-1,3-oxathiolanes) have been identified that reduce the chemotaxis and respiratory burst leading to the formation of damaging oxygen radicals or polymorphonuclear leukocytes during an inflammatory or immune response. The compounds exhibit this biological activity by acting as PAF receptor antagonists, by inhibiting the enzyme 5-lipoxygenase, or by exhibiting dual activity, i.e., by acting as both a PAF receptor antagonist and inhibitor of 5-lipoxygenase.

A method to treat disorders mediated by PAF or leukotrienes is also provided, that includes administering an effective amount of one or more of the above-identified compounds or a pharmaceutically acceptable salts or derivative thereof, optionally in a pharmaceutically acceptable carrier.

Examples of immune and allergic disorders include general inflammation, cardiovascular disorders, skeletal-muscular disorders, osteoarthritis, gout, asthma, lung edema, adult respiratory distress syndrome, pain, aggregation of platelets, rheumatoid arthritis, juvenile rheumatoid arthritis, psoriatic arthritis, psoriasis, autoimmune uveitis, allergic encephalomyelitis, systemic lupus erythematosis, acute necrotizing hemorrhagic encephalopathy, idiopathic thrombocytopenia, polychondritis, chronic active hepatitis, idiopathic sprue, Crohn's disease, Graves ophthalmopathy, primary biliary cirrhosis, uveitis posterior, interstitial lung fibrosis; allergic asthma; and inappropriate allergic responses to environmental stimuli such as poison ivy, pollen, insect stings and certain foods, including atopic dermatitis and contact dermatitis.

The compounds disclosed herein can also be used as research tools to study the structure and location of PAF receptors as well as biological pathways involving leukotrienes.

The compounds are of the formula:

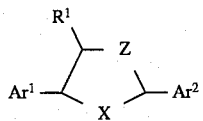

wherein $Ar^1$ and $Ar^2$ are independently:

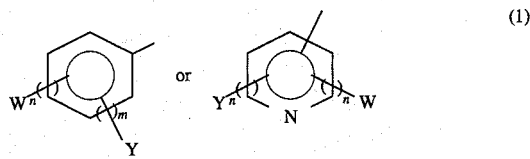

(1)

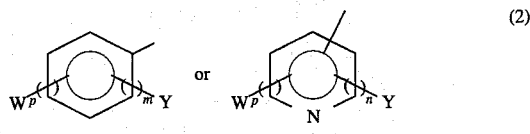

(2)

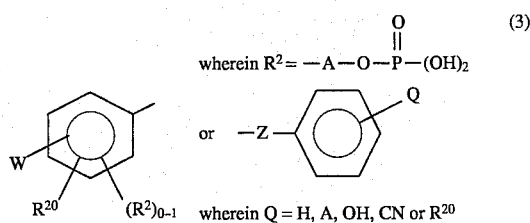

(3)

wherein $R^2 = -A-O-\overset{O}{\underset{\|}{P}}-(OH)_2$ wherein Q = H, A, OH, CN or $R^{20}$ and one of $Ar^1$ and $Ar^2$ is (1) or (3);

wherein:

X and Z are independently O or S;

W is independently:

(1) $-AN(OM)C(O)N(R^3)R^4$, $-AN(R^3)C(O)N(OM)R^4$, $-AN(OM)C(O)R^4$, $-AC(O)N(OM)R^4$, $-N(OM)C(O)N(R^3)R^4$, $-N(R^3)C(O)N(OM)R^4$, $-N(OM)C(O)R^4$, $-C(O)N(OM)R^4$, $-OR^6N(R^5)R^6-(C_5H_4N)R^6R^7$, $-OR^6N(COR^5)R^6-(C_5H_4N)R^6R^7$, $-OR^6OC(O)N(COR^5)R^6-(C_5H_4N)R^6R^7$, $-OR^6O(CO)N(CO_2R^6)R^6(C_5H_4N)R^6R^7$, $-A(C_5H_4N)R^6R^7$, or $-OR^6N(CO_2R^5)R^6-(C_5H_4N)R^6R^7$;

(2) an amidohydroxyurea of the formula: $-N(R^{19})C(O)AN(OM)C(O)NHR^{20}$, $-C(O)N(R^{19})AN(OM)C(O)NHR^{20}$, $-AN(R^{19})C(O)AN(OM)C(O)NHR^{20}$, $-AC(O)N(R^{19})AN(OM)C(O)NHR^{20}$, $-NHC(O)N(OM)A(O)N(R^{19})_2$; or $-NHC(O)N(OM)AN(R^{19})C(O)R^{19}$;

(3) an oxalkane of the structure:

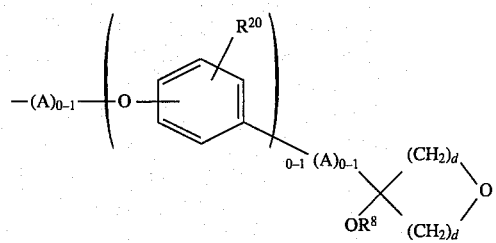

wherein d is independently 1–4;

(4) a thioalkane of the structure:

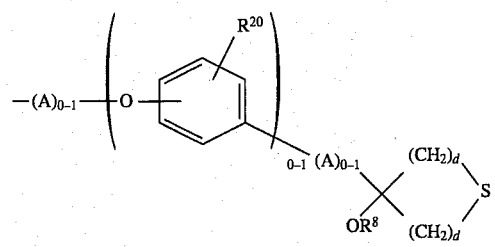

or (5) a quinolylmethoxy of the structure:

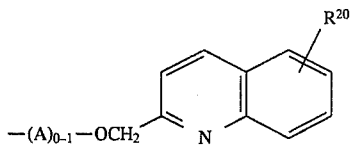

n is 1 or 2;
m is 1, 2 or 3, unless otherwise indicated;
p is 0 or 1;
A is alkyl, alkenyl, alkynyl, alkyaryl, aralkyl, halo lower alkyl, halo lower alkenyl, halo lower alkynyl, $-C_{1-10}$alkyl(oxy)$C_{1-10}$alkyl, $-C^{1-10}$alkyl(thio)$C_{1-10}$alkyl, $-N(R^3)C(O)$alkyl, $-N(R^3)C(O)$alkenyl, $-N(R^3)C(O)$alkynyl, $-N(R^3)C(O)$(alkyl)oxy(alkyl), $-N(R^3)C(O)$(alkyl)thio)alkyl), $-N(R^3)C(O)N$(alkyl), $-N(R^3)C(O)N$(alkenyl), $-N(R^3)C(O)N$(alkynyl), $-N(R^3)C(O)N$(alkyl)oxy(alkyl), $-N(R^3)C(O)N$(alkyl)thio(alkyl), $-N(R^3)C(O_2)$alkyl, $-N(R^3)C(O_2)$alkenyl, $-N(R^3)C(O_2)$alkynyl, $-N(R^3)C(O^2)$(alkyl)oxy(alkyl), $-N(R^3)C(O_2)$(alkyl)thio(alkyl), $-OC(O_2)$alkyl, $-OC(O_2)$alkenyl, $-OC(O_2)$alkynyl, $-OC(O_2)$(alkyl)oxy(alkyl), $-OC(O_2)$(alkyl)thio(alkyl), $-N(R^3)C(S)$alkyl, $-N(R^3)C(S)$alkenyl, $-N(R^3)C(S)$alkynyl, $-N(R^3)C(S)$(alkyl)oxy(alkyl), $-N(R^3)C(S)$(alkyl)thio(alkyl), $-N(R^3)C(S)N$(alkyl), $-N(R^3)C(S)N$(alkenyl), $-N(R^3)C(S)N$(alkynyl), $-N(R^3)C(S)N$(alkyl)oxy(alkyl), $-N(R^3)C(S)N$(alkyl)thio(alkyl), $-N(R^3)C(S)S$(alkyl), $-N(R^3)C(S)S$(alkenyl), $-N(R^3)C(S)S$(alkynyl), $-N(R^3)C(S)S$(alkyl)oxy(alkyl), $-N(R^3)C(S)S$(alkyl)thio(alkyl), $-SC(S)S$(alkyl), $-SC(S)S$(alkenyl), $-SC(S)S$(alkynyl), $-SC(S)S$(alkyl)oxy(alkyl), and $-SC(S)S$(alkyl)thio(alkyl);

M is hydrogen, a pharmaceutically acceptable cation, or a metabolically cleavable leaving group;

Y is independently;
(a) hydrogen;
(b) $R^{1-6}$, $R^8$, $R^{10}$, $-OR^3$, $-OR^{11}$, $-OR^{12}$, $R^3S-$, $R^5S-$, $R^3SO-$, $R^5SO-$, $R^3SO_2-$, $R^5SO_2-$, $CF_3O-$, $CF_3S-$, $CF_3SO-$, $CF_3SO_2$, $-OCH_2$oxycyclopropyl, $-OCH_2C(O)OR^3$, $-OCH_2OR^3$, $-OCH_2C(O)R^3$, $-OCH_2C_{3-8}$cycloalkyl, $-OCH_2CH(R)R^3$, $-OCH_2$cyclopropyl, $-OCH_2$ aryl, $-OCH_2CH(OH)CH_2OH$, aryl-$CH_2$$SO_2-$, $(R^3)_2CHCH_2SO_2-$, $-CH_2CH(OH)CH_2OH$, $CF_3SO_2-$, $R^3R^4N-$, $-OCH_2CO_2R^3$, $-NR^3COR^3$, $-OCONH_2$, $-OCONR^3R^4$, $-CONH_2$, $-CONR^3R^4$, $-CR^3R^3R^4$, $-SO_2NR^3R^4$, $-SONR^3R^4$, $-CH_3OCH_2NR^3R^6$, $-SNR^3R^4$, $-CO_2R^3$, $-NR^3R^4SO_2R^3$, $-NR^3R^4SOR$, $-COR^3$, $-CONR^3$, $-NO_2$, $-CN$, $-N(R^5)CONR^3R^4$, $-CH_2N(R^5)CONR^3R^4$, $-R^6NR^3R^4$, $-OR^6NR^3R^4$, $-O(O)CR^5$, $-O(O)CNR^3R^4$,

$-SR^6NR^3R^4$, $-S(O)R^6NR^3R^4$, $-SO_2R^6NR^3R^4$,

$-SR^6OH$, $-S(O)R^6OH$, $-SO_2R^6OH$, $-OR^6OC(O)N(CO_2R^6)R^6$;

(c) a heterocycle, including but not limited to, pyrryl, furyl, pyridyl; 1,2,4-thiadiazolyl; pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbozolyl, benzimidazolyl, and isoxazolyl and the like, optionally substituted with a group described in Y section (b);

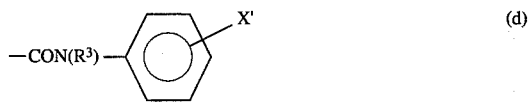

wherein X' is halo, $-C(O)$aryl, $CF_3$, or $OR^3$; $-NR_3COR^3$; $-OCONH_2$; $-CR^3R^3R^4$; $-CH_2OR^3$; $-CH_2OR^3$; $-CH_2CO_2R^3$; $-CH_2$ $OCOR^3$; $R^3CH(R^3)CH_2SO_3-$; $-NHCH_2COOR^3$; halo such as F, Cl, Br and I; $N^+R^3R^3R^4R^7$; $-NR^3SO_2R^3$ ; $COR^3$; $NO_2$; or CN; or

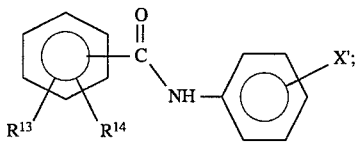

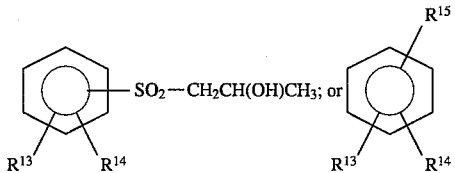

wherein $R^{13}$, $R^{14}$ and $R^{15}$ independently represents: BO— wherein B is $-CH_2-$oxacyclopropyl, $-CH_2OR^3$, $-CH_2C(O)R^3$, $-CH_2CH(R^3)R^3$, $-CH_2$Aryl, $-CH_2CH(OH)-CH_2OH$; $R^3C(R^3)_2CH_2$ $SO_2$; or $R^{13}-R^{14}$ or $R^{14}-R^{15}$ are joined together to from a bridge such as $-OCHR^2CHR^2-S(O)_n-$ wherein n is 0 to 3; or

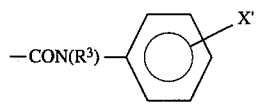

where X' is halo, $-C(O)$aryl, $-CF_3$, or $-OR^3$; $-CH_2OR^3$; $-CH_2CO_2R^3$; $-CH_2COR^3$; $-NHCH_2COOR^3$; $-N^+R^3R^3R^4R^7$.

$R^1$ is hydrogen, halogen, or lower alkyl, specifically including lower alkyl of 1-6 carbon atoms, e.g., methyl, cyclopropylmethyl, ethyl, isopropyl, butyl, pentyl and hexyl, as well as $C_{3-8}$ cycloalkyl, for example, cyclopentyl; halo lower alkyl especially $C_{1-6}$ haloalkyl, for example, trifluoromethyl; halo especially fluoro; $-COOH$; $-CONR^{16}R^{17}$ wherein $R^{16}$ and $R^{17}$ independently represent $C_{1-6}$ alkyl and hydrogen, $-COOR^3$, lower alkenyl especially $C_{2-6}$ alkenyl e.g., vinyl, allyl, $CH_3CH=CH-CH_2$ $CH_2$, and $CH_3CH_2)_3CH=CH-$; $-COR^3$; $-CH_2OR^3$; lower alkynyl especially $C_{2-6}$ alkynyl e.g., $-C\equiv CH$; $-CH_2NR^4R^3$; $-CH_2SR^3$; $=O$; $-OR^3$; or $-NR^3R^4$;

$R^3$ and $R^4$ are independently alkyl, alkenyl, alkynyl, aryl, aralkyl, alkyaryl, hydrogen, $C_{1-6}$ alkoxy-$C_{1-10}$ alkyl, $C_{1-6}$ alkylthio-$C_{1-10}$ alkyl, and $C_{1-10}$ substituted alkyl (wherein the substituent is independently hydroxy or carbonyl, located on any of $C_{1-10}$);

$R^5$ is lower alkyl, lower alkenyl, lower alkynyl, hydroxyl, hydrogen, halo lower alkyl, halo lower alkenyl, halo lower alkynyl, aralkyl, or aryl;

$R^6$ is lower alkyl, lower alkenyl, lower alkynyl, aralkyl, halo lower alkyl, halo lower alkenyl, halo lower alkynyl, or aryl;

$R^7$ is an organic or inorganic anion;

$R^8$ is halo alkyl, halo lower alkyl, halo lower alkenyl, halo lower alkynyl, lower alkenyl, lower alkynyl, aralkyl, or aryl;

$R^9$ is independently hydrogen, halogen, lower alkyl, halo lower alkyl, lower alkenyl, lower alkynyl, —$CONR^3R^4$, —$COR^5$, —$CO_2R^5$, —$CH_2OR^5$, —$CH_2NR^5$ $R^5$, —$CH_2SR^5$, =O, =$NR^5$, —$NR^3R^4$, —$NR^3R^4R^7$; or —$OR^5$;

$R^{10}$ is —$R^3$, —$R^8$, —$C(O)N(OR^3)R^3$, or —$OR^3$.

$R^{11}$ is $C_1$ to $C_{12}$ alkyl; substituted $C_1$ to $C_{12}$ alkyl wherein the substituent is selected from the group consisting of hydroxy and amino, alkenyl, lower alkoxy-alkyl; alkylcarbonylalkyl, -alkylamino, -alkylamino(alkyl or dialkyl), lower alkyl $S(O)_m$—lower alkyl in which m is 0, 1 or 2; imidazolyl lower alkyl, morpholinyl lower alkyl, thiazolinyl lower alkyl, piperidinyl lower alkyl, imidazolylcarbonyl, morpholinyl carbonyl, amorpholinyl(lower alkyl)aminocarbonyl, N-pyrrylpyridinyl-lower alkyl; pyridylthio-lower alkyl; morpholinyl-lower alkyl; hydroxyphenylthio-lower alkyl; cyanophenylthio-lower alkyl; imidazolylthio-lower alkyl; triazolylthio-lower alkyl; triazolylphenylthio-lower alkyl; tetrazolylthio-lower alkyl; tetrazolylphenylthio-lower alkyl; aminophenylthio-lower alkyl; N,N-di-substituted aminophenylthio-lower alkyl wherein the substituents each independently represent lower alkyl; amidinophenylthio-lower alkyl; phenylsulfinyl-lower alkyl; or phenylsulfonyl lower alkyl;

$R^{12}$ is alkyl; substituted alkyl wherein the substituent is selected from the group consisting of hydroxy and amino; -lower alkyl-O—$R^{18}$, wherein $R^{18}$ is —$PO_2(OH)$—$M^+$ or —$PO_3(M^+)_2$, wherein $M^+$ is a pharmaceutically acceptable cation; —$C(O)(CH_2)_2CO_2$—$M^+$, or —$SO_3$—$M^+$; -lower alkylcarbonyl-lower alkyl; -carboxy lower alkyl; -lower alkylamino-lower alkyl; N,N-di-substituted amino lower alkyl-, wherein the substituents each independently represent lower alkyl; pyridyl-lower alkyl; imidazolyl-lower alkyl; imidazolyl-Y-lower alkyl wherein Y is thio or amino; morpholinyl-lower alkyl; pyrrolidinyl-lower alkyl; thiazolinyl-lower alkyl; piperidinyl-lower alkyl; morpholinyl-lower hydroxyalkyl; N-pyrryl; piperazinyl-lower alkyl; N-substituted piperazinyl-lower alkyl, wherein the substituent is lower alkyl; triazolyl-lower alkyl; tetrazolyl-lower alkyl; tetrazolylamino-lower alkyl; or thiazolyl-lower alkyl;

$R^{19}$ is H, lower alkyl, or lower alkenyl; and $R^{20}$ is H, halogen, lower alkoxy, or lower alkyl.

The compounds disclosed herein can also be used as research tools to study the structure and location of PAF receptors as well as biological pathways involving leukotrienes.

DETAILED DESCRIPTION OF THE INVENTION

I. Description and Synthesis of the Compounds

A. Compounds

The term alkyl, as used herein, unless otherwise specified, refers to a saturated straight, branched, or cyclic hydrocarbon of $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term lower alkyl, as used herein, and unless otherwise specified, refers to a $C_1$ to $C_6$ saturated straight, branched, or cyclic (in the case of $C_{5-6}$) hydrocarbon, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term alkenyl, as referred to herein, and unless otherwise specified, refers to a straight, branched, or cyclic (in the case of $C_{5-6}$) hydrocarbon of $C_2$ to $C_{10}$ with at least one double bond.

The term lower alkenyl, as referred to herein, and unless otherwise specified, refers to an alkenyl group of $C_2$ to $C_6$, and specifically includes vinyl and allyl.

The term lower alkylamino refers to an amino group that has one or two lower alkyl substituents.

The term alkynyl, as referred to herein, and unless otherwise specified, refers to a $C_2$ to $C_{10}$ straight or branched hydrocarbon with at least one triple bond.

The term lower alkynyl, as referred to herein, and unless otherwise specified, refers to a $C_2$ to $C_6$ alkynyl group, specifically including acetylenyl and propynyl.

The term aryl, as used herein, and unless otherwise specified, refers to phenyl or substituted phenyl, wherein the substituent is halo or lower alkyl.

The term halo, as used herein, includes fluoro, chloro, bromo, and iodo.

The term halo (alkyl, alkenyl, or alkynyl) refers to a (alkyl, alkenyl, or alkynyl) group in which at least one of the hydrogens in the group has been replaced with a halogen atom.

The term aralkyl refers to an aryl group with an alkyl substituent.

The term alkaryl refers to an alkyl group that has an aryl substituent.

The term organic or inorganic anion refers to an organic or inorganic moiety that carries a negative charge and can be used as the negative portion of a salt.

The term "pharmaceutically acceptable cation" refers to an organic or inorganic moiety that carries a positive charge and that can be administered in association with a pharmaceutical agent, for example, as a countercation in a salt. Pharmaceutically acceptable cations are known to those of skill in the art, and include but are not limited to sodium, potassium, and quaternary amine.

The term "metabolically cleavable leaving group" refers to a moiety that can be cleaved in vivo from the molecule to which it is attached, and includes but is not limited to an organic or inorganic anion, a pharmaceutically acceptable cation, acyl (for example (alkyl)C(O), including acetyl, propionyl, and butyryl), alkyl, phosphate, sulfate and sulfonate.

The term "enantiomerically enriched composition or compound" refers to a composition or compound that includes at least 95% by weight of a single enantiomer of the compound.

The term pharmaceutically active derivative refers to any compound that upon administration to the recipient, is capable of providing directly or indirectly, the compounds disclosed herein.

B. Stereochemistry

The 2,4-diaryl-1,3-dithiolanes; 2,4-diaryl-1,3-dioxolanes; 2,4-diaryl-1,3-oxathiolanes; and 2,5-diaryl-1,3-oxathiolanes disclosed herein exhibit a number of stereochemical configurations. Carbon atoms 2 and 4 (or 2 and 5, as appropriate) in the center ring are chiral, and thus the center ring exists at a minimum as a diastereomeric pair. Each diastereomer exists as a set of enantiomers. Therefore, based on the chiral $C_2$ and $C_4$ (or $C_2$ and $C_5$, as appropriate) atoms alone, the compound is a mixture of four enantiomers.

If a nonhydrogen substituent is located on the carbon atom to which $R^1$ in the center ring, then the $C_5$ atom is also chiral, that is again a mixture of two enantiomers.

The R groups in the active compounds described herein can likewise include chiral carbons, and thus, optically active centers.

It is sometimes found that one or more enantiomers of a biologically active compound is more active, and perhaps less toxic, than other enantiomers of the same compound. Such enantiomerically enriched compounds are often preferred for pharmaceutical administration to humans. For example, it has been discovered that trans-2,5-diaryl tetrahydrothiophene and trans-2,5-diaryl tetrahydrofuran are often more active PAF receptor antagonists than their cis counterparts.

One of ordinary skill in the art can easily synthesize and separate the enantiomers of the disclosed compounds using chiral reagents and known procedures, and can evaluate the biological activity of the isolated enantiomer using methods disclosed herein or otherwise known. Through the use of chiral NMR shift reagents, polarimetry, or chiral HPLC, the optical enrichment of the compound can be determined.

Classical methods of resolution include a variety of physical and chemical techniques. Often the simplest and most efficient technique is repeated recrystallization. Recrystallization can be performed at any stage in the preparation of the compound, or the final enantiomeric product. If successful, this simple approach represents a method of choice.

When recrystallization fails to provide material of acceptable optical purity, other methods can be evaluated. If the compound is basic, one can use chiral acids that form diastereomeric derivative that may possess significantly different solubility properties. Nonlimiting examples of chiral acids include malic acid, mandelic acid, dibenzoyl tartaric acid, 3-bromocamphor-8-sulfonic acid, 10-camphorsulfonic acid, and di-p-toluoyltartaric acid. Similarly, acylation of a free hydroxyl group with a chiral acid also results in the formation of diastereomeric derivatives whose physical properties may differ sufficiently to permit separation.

Enantiomerically pure or enriched compounds can be obtained by passing the racemic mixture through a chromatographic column that has been designed for chiral separations, including cyclodextrin bonded columns marketed by Rainin Corporation.

A variety of chemical reagents and experimental procedures have been developed in recent years to produce enantiomerically pure or enriched products. For example, individual 2S,5S or 2R,5R enantiomers of 2,5-diaryl tetrahydrofurans can be prepared by the method described by Corey et al. (Corey, E. J. et al., *Tetrahedron Letters* 29, 2899 (1988)). Enantiomerically pure or enriched 2,4-diaryl-1,3-dithiolanes; 2,4-diaryl-1,3-dioxolanes; 2,4-diaryl-1,3-oxathiolanes; and 2,5-diaryl-1,3-oxathiolanes can be prepared in an analogous fashion.

C. Syntheses of Active Compounds

The 2,4-diaryl-1,3-dithiolanes; 2,4-diaryl-1,3-dioxolanes; 2,4-diaryl-1,3-oxathiolanes; and 2,5-diaryl-1,3-oxathiolanes disclosed herein can be prepared in a variety of ways known to those skilled in the art. Exemplary methods for preparing 2,4-diaryl-1,3-dithiolanes are disclosed in detail in Example 1 and Schemes 1–5 below. Exemplary methods for preparing 2,5-diaryl-1,3-oxathiolanes are provided in Scheme 6 below. 2,4-Diaryl-1,3-dioxolanes and 2,4-diaryl-1,3-oxathiolanes can be prepared analogously. 2,4-Diaryl-1,3-dioxalanes can also be prepared by the methods disclosed by Corey, et al., Tetrahedron Letters, 29, 2899–2909 (1988); and Ko, et al., Tetrahedron, 40, 1333–1343 (1984). 2,4-Diaryl-1,3-oxathiolanes and 2,5-diaryl-1,3-oxathiolanes can be prepared by the condensation of $Ar^2C(O)H$ with $Ar^1CH(OH)CH_2SH$ and $Ar^1CH(SH)CH_2OH$. Care should be taken to avoid significantly acidic pH when preparing and handling the dioxolane derivatives.

The amidohydroxyurea, oxalkane, thioalkane, and quinolylmethoxy substitutes can be added to the 2,4-diaryl-1,3-dithiolanes; 2,4-diaryl-1,3-dioxolanes; 2,4-diaryl-1,3-oxathiolanes; and 2,5-diaryl-1,3-oxathiolanes by methods known to those skilled in the art, including the procedures described below.

A general procedure for preparing a hydroxyurea is:

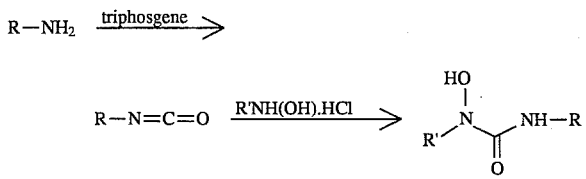

wherein R is a 2,4-diaryl-1,3-dithiolanes; 2,4-diaryl-1,3-dioxolanes; 2,4-diaryl-1,3-oxathiolanes; and 2,5-diaryl-1,3-oxathiolanes; with or without a linking moiety, and R' is a moiety as defined in detail above.

General procedures for preparing reverse hydroxyureas are:

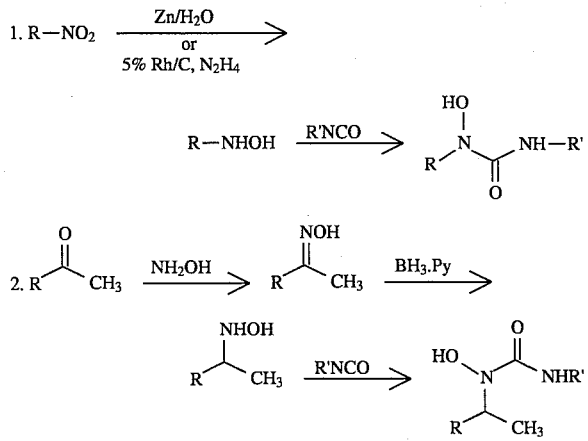

A general procedure for preparing a hydroxamic acid is:

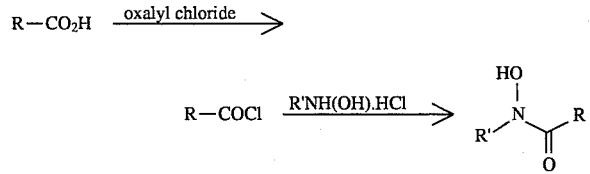

A general procedure for preparing a reverse hydroxamic acid is:

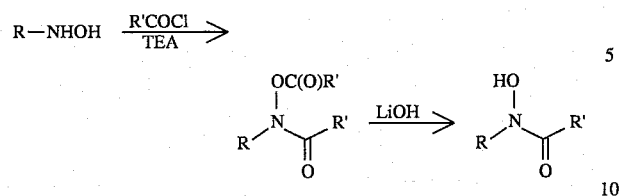

A general procedure for preparing amidohydroxyurea moieties is:

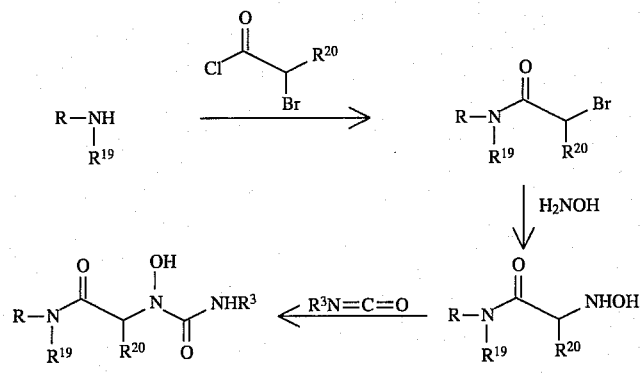

Oxaalkanes and thioalkanes can be prepared as described by Crawley, et al., *J. Med. Chem.*, 35, 2600–2609 (1992), and illustrated below, by conversion of the desired moiety into a Grignard reagent or lithium salt, followed by reaction with the appropriate cyclic ketone.

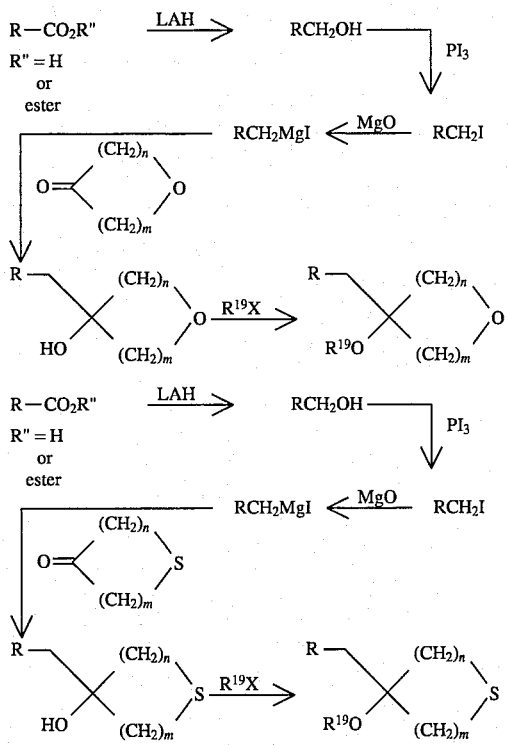

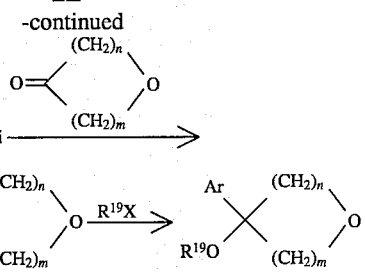

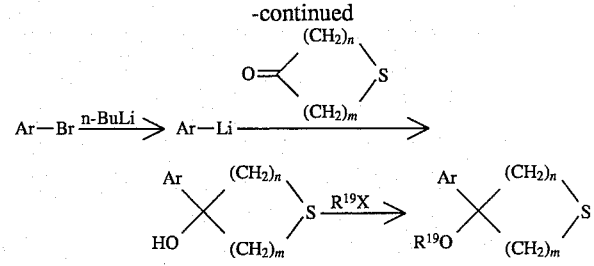

Quinolylmethoxy moieties can be prepared as described by Musser, et al., *J. Med. Chem.*, 35, 2501–2524 (1992), and references cited therein, as illustrated below.

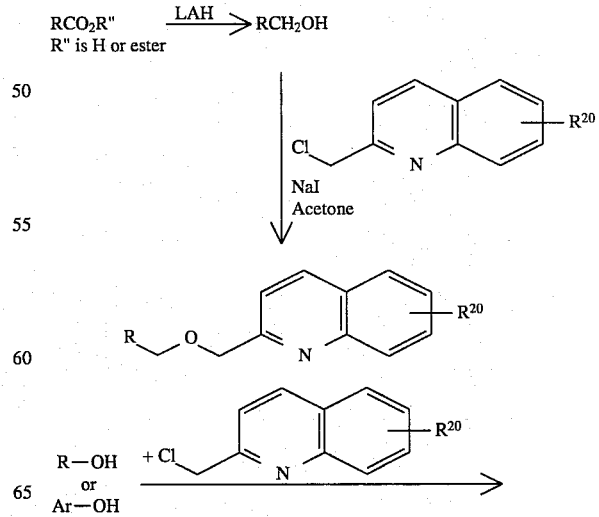

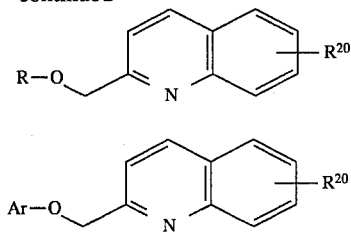

EXAMPLE 1

Preparation of Cis and Trans-2-[3,4-dimethoxy-5-(N-hydroxy-N-methylureidyl) phenyl]-4 -(3,4,5-trimethoxyphenyl)-1,3-dithiolane (1)

Trans-2-(5-amino-3,4-dimethoxyphenyl)-4-(3,4,5-trimethoxyphenyl)-1,3-dithiolane (23) (0.150 g, 0.355 mmole), triethylamine (50 mg), triphosgene (0.035 g, 0.118 mmole), and 20 ml dry dichloromethane were refluxed for 2 hours under an argon atmosphere. When all of the amine had been converted to isocyanate by TLC, the reaction was cooled to room temperature and N-methylhydroxylamine hydrochloride (0.044 g, 0.533 mmole) predissolved in 5 ml THF, 75 ml triethylamine, and 0.5 ml $H_2O$ was added. The reaction was stirred at room temperature overnight under an argon atmosphere. The solvent was removed in vacuo, and the remaining oil was redissolved in dichloromethane. The organic layer was washed with $H_2O$, dried over $MgSO_4$, and concentrated to an oil in vacuo which was purified by flash column chromatography with 2:1 hexane/ethyl acetate as eluent. (112 mg, 64% yield: foam). The product can be crystallized from hexane/ethyl acetate to a white solid.

Trans epimer: $^1$H NMR (300 MHz, $CDCl_3$) d 3.28 (s, 3H, $NCH_3$), 3.45 (dd, 1H, C-5 CH), 3.65 (dd, 1H, C-5 CH), 3.84 (s, 3H, $OCH_3$), 3.85 (s, 3H, $OCH_3$), 3.88 (s, 6H, $OCH_3$), 3.90 (s, 3H, $OCH_3$), 5.09 (dd, 1H, C-4 CH), 5.72 (s, 1H, C-2 CH), 6.72 (s, 2H, ArH), 6.90 (d, 1H, ArH), 8.15 (d, 1H, ArH), 8.52 (s, 1H, ArNHC(O)); MS (IBu) m/e: 497 ($M^+$).

mp: 93°–94° C. (EtOAc/hexane); Anal Calcd for $C_{22}H_{28}O_7S_2N_2$: C, 53.21; H, 5.68; S, 12.91; N, 5.66. Found: C, 53.31; H, 5.70; S, 12.84; N, 5.60.

The cis product can be obtained in the same manner as above starting from cis-2-(5-amino-3,4-dimethoxyphenyl)-4-(3,4,5-trimethoxyphenyl)-1,3-dithiolane (23).

Cis epimer: $^1$H NMR (300 MHz, $CDCl_3$) d 3.25 (s, 3H, $NCH_3$), 3.55 (d, 2H, C-5 $CH_2$), 3.83 (s, 3H, $OCH_3$), 3.84 (s, 3H, $OCH_3$), 3.88 (s, 9H, $OCH_3$), 4.84 (dd, 1H, C-4 CH), 5.71 (s, 1H, C-2 CH), 6.78 (s, 2H, ArH), 6.89 (d, 1H, ArH), 8.23 (d, 1H, ArH), 8.52 (s, 1H, ArNHC(O)); MS (CI) m/e: 497 ($M^+$) 450, 424, 227, 147.

Preparation of Trans-2-[3,4-dimethoxy-5-(N-hydroxy-N-methylthioureidyl)phenyl-4 -(3,4,5-trimethoxyphenyl)-1,3-dithiolane (2)

Trans-2-(5-amino-3,4-dimethoxyphenyl)-4-(3,4,5-trimethoxyphenyl)-1,3-dithiolane (23) (0.150 g, 0.355 mmole), triethylamine (36 mg), thiocarbonyldiimidazole (0.085 g, 0.355 mmole), and 10 ml dry dichloromethane were stirred at room temperature for 30 minutes followed by reflux for 1 hour under an argon atmosphere. All of the amine had been converted to the isothiocyanate by TLC. The reaction was cooled to room temperature and N-methylhydroxylamine hydrochloride (0.042 g, 0.500 mmole) predissolved in 5 ml THF, 50 mg triethylamine, and 0.5 ml $H_2O$ was added. The reaction was stirred at room temperature overnight under an argon atmosphere. The solvent was removed in vacuo, and the remaining oil was redissolved in dichloromethane. The organic layer was washed with $H_2O$, dried over $MgSO_4$, and concentrated to an oil in vacuo which was purified by flash column chromatography with 2:1 hexane/ethyl acetate as eluent. (125 mg, 69% yield: foam).

Trans epimer: $^1$H NMR (300 MHz, $CDCl_3$) 3.46 (dd, 1H, C-5 CH), 3.67 (dd, 1H, C-5 CH), 3.72 (s, 3H, $NCH_3$), 3.84 (s, 3H, $OCH_3$), 3.85 (s, 3H, $OCH_3$), 3.88 (s, 6H, $OCH_3$), 3.90 (s, 3H, $OCH_3$), 5.09 (dd, 1H, C-4 CH), 5.81 (s, 1H, C-2 CH), 6.74 (s, 2H, ArH), 6.95 (d, 1H, ArH), 8.48 (d, 1H, ArH), 9.03 (s, 1H, ArNHC(S)).

Preparation of Trans-2-[3,4-dimethoxy-5-(N-n-butyl-N-hydroxyureidyl)phenyl]-4-(3,4,5 -trimethoxyphenyl)-1,3-dithiolane (3)

Trans-2-(5-amino-3,4-dimethoxyphenyl)-4-(3,4,5-trimethoxyphenyl)-1,3-dithiolane (23) (0.080 g, 0.189 mmole), triethylamine (29 mg), triphosgene (0.025 g, 0.085 mmole), and 10 ml dry dichloromethane were refluxed for 1 hour under an argon atmosphere. When all of the amine had been converted to isocyanate by TLC, the reaction was cooled to room temperature and N-butylhydroxylamine (0.020 g, 0.200 mmole) was added. The reaction was stirred at room temperature overnight under an argon atmosphere. The solvent was removed in vacuo, and the remaining oil was redissolved in dichloromethane. The organic layer was washed with $H_2O$, dried over $MgSO_4$, and concentrated to an oil in vacuo which was purified by flash column chromatography with 2:1 hexane/ethyl acetate as eluent. (35 mg, 34% yield: oil).

Trans epimer: $^1$H NMR (300 MHz, $CDCl_3$) 0.95 (t, 3H, $CH_3$), 1.24 (m, 2H, $CH_2$), 1.61 (m, 2H, $CH_2$), 3.45 (dd, 1H, C-5 CH), 3.62 (t, 2H, $NCH_2$), 3.65 (dd, 1H, C-5 CH), 3.84 (s, 3H, $OCH_3$), 3.85 (s, 3H, $OCH_3$), 3.88 (s, 6H, $OCH_3$), 3.90 (s, 3H, $OCH_3$), 5.09 (dd, 1H, C-4 CH), 5.82 (s, 1H, C-2 CH), 6.72 (s, 2H, ArH), 6.91 (d, 1H, ArH), 8.15 (d, 1H, ArH), 8.54 (s, 1H, ArNHC(O)).

Preparation of Cis and Trans-2-[3,4-dimethoxy-5-(N-t-butyl-N-hydroxyureidyl)phenyl]-4 -(3,4,5-trimethoxyphenyl)-1,3-dithiolane (4)

Dithiolane (4) was synthesized following substantially the same procedure as for hydroxyureas 1 and 3.

Trans epimer: $^1$H NMR (300 MHz, $CDCl_3$) 1.23 (s, 9H, $CH_3$), 3.45 (dd, 1H, C-5 CH), 3.64 (dd, 1H, C-5 CH), 3.84 (s, 3H, $OCH_3$), 3.85 (s, 3H, $OCH_3$), 3.89 (s, 6H, $OCH_3$), 3.91 (s, 3H, $OCH_3$), 5.10 (dd, 1H, C-4 CH), 5.84 (s, 1H, C-2 CH), 6.73 (s, 2H, ArH), 6.97 (d, 1H, ArH), 8.08 (d, 1H, ArH), 8.71 (s, 1H, ArNHC(O)).

Preparation of Trans-2-[4-allyloxy-3-methoxy-5-(N-hydroxy-N-methylureidyl)phenyl]-4 -(3,4,5-trimethoxyphenyl)-1,3-dithiolane (5)

Trans-2-(4-allyloxy-5-amino-3-methoxyphenyl)-4-(3,4, 5-trimethoxphenyl)-1,3-dithiolane (25) (1.0 g, 2.23 mmole), triethylamine (0.225 g), triphosgene (0.264 g, 0.890 mmole), and 25 ml dry dichloromethane were refluxed for 3 hours under an argon atmosphere. two products had formed by TLC, however, the reaction was cooled to room temperature and N-methylhydroxylamine hydrochloride (0.595 g, 6.69 mmole) predissolved in THF/H$_2$O/Et$_3$N (5 ml/0.5/ml/595 mg) was added. The reaction was stirred at room temperature overnight under an argon atmosphere. The solvent was removed in vacuo, and the remaining oil was redissolved in dichloromethane. The organic layer was washed with H$_2$O, dried over MgSO$_4$, and concentrated to an oil in vacuo which was purified by flash column chromatography with 2:1–1:1 hexane/ethyl acetate as eluent. (314 mg: foam).

Trans epimer: $^1$H NMR (300 MHz, CDCl$_3$) 3.26 (s, 3H, CH$_3$), 3.45 (dd, 1H, C-5 CH), 3.65 (dd, 1H, C-5 CH), 3.84 (s, 3H, OCH$_3$), 3.89 (s, 6H, OCH$_3$), 3.90 (s, 3H, OCH$_3$), 4.52 (d, 2H, OCH$_2$), 5.09 (dd, 1H, C-4 CH), 5.30 (dd, 2H, CH$_2$=), 5.83 (s, 1H, C-2 CH), 6.06 (m, 1H, CH=), 6.73 (s, 2H, ArH), 6.90 (d, 1H, ArH), 8.15 (d, 1H, ArH), 8.61 (s, 1H, ArNHC(O)).

Preparation of
Trans-2-[4-allyloxy-3-methoxy-5-(N-t-butyl-N-hydroxyureidyl)phenyl]-4-(3,4,5-trimethoxyphenyl)-1,3-dithiolane (6)

Dithiolane (6) was synthesized following substantially the same procedure as for hydroxyurea 5.

Trans epimer: $^1$H NMR (300 MHz, CDCl$_3$) 1.21 (s, 9H, CH$_3$), 3.45 (dd, 1H, C-5 CH), 3.65 (dd, 1H, C-5 CH), 3.84 (s, 3H, OCH$_3$), 3.89 (s, 6H, OCH$_3$), 3.90 (s, 3H, OCH$_3$), 4.54 (d, 2H, OCH$_2$), 5.10 (dd, 1H, C-4 CH), 5.30 (dd, 2H, CH$_2$=), 5.85 (s, 1H, C-2 CH), 6.05 (m, 1H, CH=), 6.74 (s, 2H, ArH), 6.97 (d, 1H, ArH), 8.15 (d, 1H, ArH), 8.77 (s, 1H, ArNHC(O)).

Preparation of
Trans-2-[4-{2-(4'-hydroxyphenylthio)ethoxy}-3-methoxy-5-nitrophenyl]-4-(3,4,5-trimethoxyphenyl)-1,3-dithiolane (7)

trans-2-[4-{2-(methanesulfonyloxy)ethoxy}-3-methoxy-5-nitrophenyl]-4 -(3,4,5-trimethoxyphenyl)-1,3-dithiolane (28) (0.570 g, 1.02 mmole), 4-hydroxythiophenol (0.384 g, 3.05 mole), triethylamine (0.308 g, 3.05 mmole) and 2 ml of THF was dissolved under an argon atmosphere. To this solution was added 20 ml ethanol and the reaction was refluxed for 12 hours. The reaction was cooled to room temperature and acidified with 10% HCl. The product was extracted into ethyl acetate, washed with H$_2$O, dried over MgSO$_4$, and concentrated to an oil in vacuo which was purified by flash column chromatography with 2:1 hexane/ethyl acetate as eluent. (420 mg, 70% yield: oil).

Trans epimer: $^1$H NMR (300 MHz, CDCl$_3$) 3.20 (t, 2H, SCH$_2$), 3.49 (dd, 1H, C-5 CH), 3.65 (dd, 1H, C-5 CH), 3.85 (s, 3H, OCH$_3$), 3.89 (s, 9H, OCH$_3$), 4.22 t, 2H, OCH$_2$), 5.04 (dd, 1H, C-4 CH), 5.78 (s, 1H, C-2 CH), 6.71 (s, 2H, ArH), 6.79 (d, 2H, ArH), 7.29 (d, 1H, ArH), 7.35 (d, 2H, ArH), 7.58 (d, 1H, ArH).

Preparation of
Trans-2-[5-amino-4-{2-(4'-hydroxyphenylthio)ethoxy}-3-methoxyphenyl]-4-(3,4,5-trimethoxyphenyl)-1,3-dithiolane (8)

Trans-2-[4-{2-(4'-hydroxyphenylthio)ethoxy}-3-methoxy-5-nitrophenyl]-4 -(3,4,5-trimethoxyphenyl)-1,3-dithiolane (7) (0.400 g, 0.677 mmole) was predissolved in 20 ml absolute ethanol. To this solution was added calcium chloride (0.075 g, 0.677 mmole) predissolved in 4 ml H$_2$O followed by freshly activated zinc dust (0.855 g, 13.54 mmole). The reaction was refluxed overnight. The solid was removed by vacuum filtration through celite and was washed with ethyl acetate. The filtrate was washed with H$_2$O, dried over MgSO$_4$, and evaporated in vacuo to a tan foam (0.326 g, 86%).

Trans epimer: $^1$H NMR (300 MHz, CDCl$_3$) 3.14 (t, 2H, SCH$_2$), 3.47 (dd, 1H, C-5 CH), 3.63 (dd, 1H, C-5 CH), 3.83 (s, 3H, OCH$_3$), 3.84 (s, 3H, OCH$_3$), 3.87 (s, 6H, OCH$_3$), 4.15 (t, 2H, OCH$_2$), 5.05 (dd, 1H, C-4 CH), 5.75 (s, 1H, C-2 CH), 6.66 (d, 1H, ArH), 6.71 (d, 1H, ArH), 6.72 (s, 2H, ArH), 6.80 (d, 2H, ArH), 7.34 (d, 2H, ArH).

Preparation of
Trans-2-[5-(N-hydroxy-N-methylureidyl)-4-{2-(4'-hydroxy-phenylthio)ethoxy}-3-methoxyphenyl]-4-(3,4,5-trimethoxyphenyl)-1,3-dithiolane (9)

Trans-2-[5-amino-4-{2-(4'-hydroxyphenylthio)ethoxy}-3-methoxy-phenyl]-4-(3,4,5 -trimethoxyphenyl)-1,3-dithiolane (8) (0.098 g, 0.175 mmole), triethylamine (40 mg), triphosgene (0.019 g, 0.065 mmole), and 10 ml dry dichloromethane were refluxed for 1 hour under an argon atmosphere. When all of the amine had been converted to isocyanate by TLC, the reaction was cooled to room temperature and N-methylhydroxylamine hydrochloride (0.019 g, 0.210 mmole) predissolved in THF/H$_2$O/Et$_3$N (5 ml/0.5/ml/595 mg) was added. The reaction was stirred at room temperature overnight under an argon atmosphere. The organic layer was washed with 5% HCl, dried over MgSO$_4$, and concentrated to an oil in vacuo which was purified by flash column chromatography with 1:1 hexane/ethyl acetate as eluent. (37 mg, 34% yield: oil).

Trans epimer: $^1$H NMR (300 MHz, CDCl$_3$) 3.09 (t, 2H, SCH$_2$), 3.25 (s, 3H, NCH$_3$), 3.47 (dd, 1H, C-5 CH), 3.63 (dd, 1H, C-5 CH), 3.85 (s, 6H, OCH$_3$), 3.88 (s, 6H, OCH$_3$), 4.14 (t, 2H, OCH$_2$), 5.07 (dd, 1H, C-4 CH), 5.82 (s, 1H, C-2 CH), 6.72 (s, 2H, ArH), 6.76 (d, 2H, ArH), 6.87 (d, 1H, ArH), 7.28 (d, 2H, ArH), 8.15 (d, 1H, ArH), 8.77 (s, 1H, ArNHC(O)).

Preparation of
Trans-2-[5-(N-(p-chlorophenyl)-N-hydroxyureidyl)-4-{2-(4'-hydroxy-phenylthio)ethoxy}-3-methoxyphenyl]-4-(3,4,5-trimethoxyphenyl)-1,3-dithiolane (10)

Trans-2-[5-amino-4-{2-(4'-hydroxyphenylthio)ethoxy}-3-methoxy-phenyl]-4 -(3,4,5-trimethoxyphenyl)-1,3-dithiolane (8) (0.085 g, 0.150 mmole), triethylamine (20 mg), triphosgene (0.017 g, 0.056 mmole), and 10 ml dry dichloromethane were refluxed for 2 hours under an argon atmosphere. When all of the amine had been converted to isocyanate by TLC, the reaction was cooled to room temperature and 4-chlorophenylhydroxylamine (0.021 g, 0.150 mmole) predissolved in CH$_2$Cl$_2$ was added. The reaction was stirred at room temperature overnight under an argon atmosphere. The organic layer was washed with 10% HCl, dried over MgSO$_4$, and concentrated to an oil in vacuo which was purified twice by flash column chromatography with 2:1 hexane/ethyl acetate as eluent. (22 mg, 20% yield: oil).

Trans epimer: ¹H NMR (300 MHz, CDCl₃) 3.12 (t, 2H, SCH₂), 3.45 (dd, 1H, C-5 CH), 3.64 (dd, 1H, C-5 CH), 3.84 (s, 3H, OCH₃), 3.86 (s, 3H, OCH₃), 3.88 (s, 6H, OCH₃), 4.18 (t, 2H, OCH₂), 5.08 (dd, 1H, C-4 CH), 5.81 (s, 1H, C-2 CH), 6.72 (s, 2H, ArH), 6.76 (m, 4H, ArH), 6.89 (d, 1H, ArH), 7.30 (d, 2H, ArH), 7.51 (d, 2H, ArH), 8.13 (d, 1H, ArH), 8.93 (s, 1H, ArNHC(O)).

Preparation of
Trans-2-[4-{2-(4'-cyanophenylthio)ethoxy}-3-methoxy-5-nitrophenyl]-4
-(3,4,5-trimethoxphenyl)-1,3-dithiolane (11)

Trans-2-[4-{2-(4'-bromophenylthio)ethoxy}-3-methoxy-5-nitrophenyl]-4 -(3,4,5-trimethoxyphenyl)-1,3-dithiolane (29) (0.420 g, 0.642 mmole), copper cyanide (0.548 g, 6.42 mmole), and 10 ml dry DMF were stirred for 24 hours under an argon atmosphere at 140° C. The reaction was cooled to room temperature and the copper was removed by filtration through celite. The copper was extensively washed with ethyl acetate and the filtrate subsequently washed with H₂O, dried over MgSO₄, and concentrated to a yellow oil in vacuo. The oil was purified by flash column chromatography with 2:1 hexane/ethyl acetate as eluent. (91 mg, 24% yield: foam). Significant quantities of starting material were recovered from the reaction mixture.

Trans epimer: ¹H NMR (300 MHz, CDCl₃) 3.42 (t, 2H, SCH₂), 3.47 (dd, 1H, C-5 CH), 3.64 (dd, 1H, C-5 CH), 3.85 (s, 3H, OCH₃), 3.86 (s, 6H, OCH₃), 3.89 (s, 3H, OCH₃), 4.32 (t, 2H, OCH₂), 5.05 (dd, 1H, C-4 CH), 5.79 (s, 1H, C-2 CH), 6.72 (s, 2H, ArH), 7.33 (d, 1H, ArH), 7.40 (d, 2H, ArH), 7.55 (d, 2H, ArH), 7.59 (d, 1H, ArH).

FT - IR (neat, cm⁻¹) 2225.

Preparation of
Trans-2-[5-amino-4-{2-(4'-hydroxyphenylthio)ethoxy}-3
-methoxyphenyl]-4-(3,4,5-trimethoxyphenyl)-1,3-dithiolane (12)

Trans-2-[4-{2-(4'-cyanophenylthio)ethoxy}-3-methoxy-5-nitrophenyl]-4 -(3,4,5-trimethoxyphenyl)-1,3-dithiolane (11) (0.091 g, 0.152 mmole) was predissolved in 10 ml absolute ethanol. To this solution was added calcium chloride (0.017 g, 0.152 mmole) predissolved in 2 ml H₂O followed by freshly activated zinc dust (0.198 g, 3.03 mmole). The reaction was refluxed for 12 hours. The zinc was removed by vacuum filtration through celite and was washed with ethyl acetate. The filtrate was washed with H₂O, dried over MgSO₄, and evaporated in vacuo to a white foam (0.071 g, 82%).

Trans epimer: ¹H NMR (300 MHz, CDCl₃) 3.35 (t, 2H, SCH₂), 3.46 (dd, 1H, C-5 CH), 3.63 (dd, 1H, C-5 CH), 3.84 (s, 6H, OCH₃), 3.88 (s, 6H, OCH₃), 4.20 (t, 2H, OCH₂), 5.05 (dd, 1H, C-4 CH), 5.74 (s, 1H, C-2 CH), 6.55 (d, 1H, ArH), 6.64 (d, 1H, ArH), 6.72 (s, 2H, ArH), 7.38 (d, 2H, ArH), 7.53 (d, 2H, ArH).

FT - IR (neat, cm⁻¹) 2225.

Preparation of
Trans-2-[5-(N-hydroxy-N-methylureidyl)-4-{2-(4'-cyano-phenylthio)ethoxy}-3
-methoxyphenyl]-4-(3,4,5-trimethoxyphenyl)-1,3-dithiolane (13)

Trans-2-[5-amino-4-{2-(4'-cyanophenylthio)ethoxy}-3-methoxyphenyl]-4-(3,4,5 -trimethoxyphenyl)-1,3-dithiolane (12) (0.060 g, 0.105 mmole), triethylamine (22 mg), triphosgene (0.037 g, 0.065 mmole), and 10 ml dry dichloromethane were refluxed for 1 hour under an argon atmosphere. When all of the amine had been converted to isocyanate by TLC, the reaction was cooled to room temperature and N-methylhydroxylamine hydrochloride (0.028 g, 0.315 mmole) predissolved in THF/H₂O/Et₃N (5 ml/0.5/ml/32 mg) was added. The reaction was stirred at room temperature overnight under an argon atmosphere. The organic layer was washed with 10% HCl, dried over MgSO₄, and concentrated to an oil in vacuo which was purified by flash column chromatography with 1:1 hexane/ethyl acetate as eluent. (31 mg, 46% yield: oil).

Trans epimer: ¹H NMR (300 MHz, CDCl₃) 3.24 (s, 3H, NCH₃), 3.33 (t, 2H, SCH₂), 3.47 (dd, 1H, C-5 CH), 3.63 (dd, 1H, C-5 CH), 3.83 (s, 3H, OCH₃), 3.84 (s, 3H, OCH₃), 3.88 (s, 6H, OCH₃), 4.23 (t, 2H, OCH₂), 5.07 (dd, 1H, C-4 CH), 5.82 (s,1H, C-2 CH), 6.73 (s, 2H, ArH), 6.89 (d, 1H, ArH), 7.33 (d, 2H, ArH), 7.52 (d, 2H, ArH), 8.13 (d, 1H, ArH), 8.60 (s, 1H, ArNHC(O)).

FT - IR (neat, cm⁻¹) 2226.

Preparation of
Trans-2-[5-(N,N-dimethylamino)-4-{2-(4'-hydroxyphenylthio)ethoxy}-3
-methoxyphenyl]-4-(3,4,5-trimethoxyphenyl)-1,3-dithiolane (14)

Trans-2-[5-amino-4-{2-(4'-hydroxyophenylthio)ethoxy}-3-methoxy-phenyl]-4 -(3,4,5-trimethoxyphenyl)-1,3-dithiolane (8) (0.015 g, 0.026 mmole), formaldehyde (21 mg), sodium cyanoborohydride (5 mg, 0.079 mmole), 10 µl acetic acid and 10 ml acetic acid were stirred for 48 hours under an argon atmosphere at room temperature. The reaction was quenched with 10% NaHCO₃ and the product was extracted into dichloromethane, dried over MgSO₄, and concentrated to an oil in vacuo which was purified by flash column chromatography with 2:1 hexane/ethyl acetate as eluent. (9 mg, 57% yield: oil).

Trans epimer: ¹H NMR (300 MHz, CDCl₃) 2.80 (s, 3H, N(CH₃)₂), 3.15 (t, 2H, SCH₂), 3.47 (dd, 1H, C-5 CH), 3.63 (dd, 1H, C-5 CH), 3.83 (s, 3H, OCH₃), 3.84 (s, 3H, OCH₃), 3.88 (s, 6H, OCH₃), 4.06 (t, 2H, OCH₂), 5.07 (dd, 1H, C-4 CH), 5.82 (s, 1H, C-2 CH), 6.73 (m, 3H, ArH), 6.76 (d, 2H, ArH), 6.82 (d, 1H, ArH), 7.29 (d, 2H, ArH).

Preparation of Trans-2-[4-allyloxy-5-{N-(m-chloromethylbenzoyloxy)-N-methylureidyl}-3
-methoxyphenyl]-4-(3,4,5-trimethoxyphenyl)-1,3-dithiolane (15)

Trans-2-[4-allyloxy-3-methoxy-5-(N-hydroxy-N-methylureidyl)phenyl]-4-(3,4,5 -trimethoxyphenyl)-1,3-dithiolane (5, CMI-03-244DG) 0.193 g, 0.370 mmole), pyridine (22 mg, 0.407 mmole), 3-chloromethylbenzoylchloride (0.070 g, 0.370 mmole), and 10 ml dry dichloromethane were stirred at room temperature for 12 hours under an argon atmosphere. The solvent was removed in vacuo, and the remaining oil was purified by flash column chromatography with 2:1–1:1 hexane/ethyl acetate as eluent. (126 mg, 46% yield: clear oil).

Trans epimer: ¹H NMR (300 MHz, CDCl₃) 3.44 (s, 3H, CH₃), 3.47 (dd, 1H, C-5 CH), 3.65 (dd, 1H, C-5 CH), 3.84 (s, 3H, OCH₃), 3.89 (s, 6H, OCH₃), 3.90 (s, 3H, OCH₃), 4.35 (d, 2H, OCH₂), 4.66 (s, 2H, CH₂Cl), 4.90 (dd, 2H, CH₂=), 5.09 (dd, 1H, C-4 CH), 5.65 (m, 1H, CH=), 5.83 (s, 1H, C-2 CH), 6.74 (s, 2H, ArH), 6.91 (d, 1H, ArH), 7.55

(t, 1H, ArH), 7.74 (dt, 1H, ArH), 7.98 (bs, 1H, ArNHC(O)), 8.08 (dt, 1H, ArH), 8.14 (m, 1H, ArH), 8.17 (d, 1H, ArH).

Preparation of Trans-2-[3,4-dimethoxy-5-{N-(p-chloromethylbenzoyl-oxy)-N-methylureidyl} phenyl]-4 -(3,4,5-trimethoxyphenyl)-1,3-dithiolane (16)

Trans-2-[3,4-dimethoxy-5-(N-hydroxy-N-methylureidyl)phenyl]-4-(3,4,5-trimethoxyphenyl)-1,3 -dithiolane (1) (0.100 g, 0.202 mmole), pyridine (22 µl), 4-chloromethylbenzoylchloride (0.039 g, 0.206 mmole), and 10 ml dry dichloromethane were stirred at room temperature for 12 hours under an argon atmosphere. The solvent was removed in vacuo, and the remaining oil was purified by flash column chromatography with 2:1 hexane/ethyl acetate as eluent. (104 mg, 79% yield: clear oil).

Trans epimer: $^1$H NMR (300 MHz, CDCl$_3$) d 3.45 (s, 3H, NCH$_3$), 3.46 (dd, 1H, C-5 CH), 3.65 (dd, 1H, C-5 CH), 3.85 (s, 3H, OCH$_3$), 3.88 (s, 3H, OCH$_3$), 3.89 (s, 9H, OCH$_3$), 4.65 (s, 2H, CH$_2$Cl), 5.09 (dd, 1H, C-4 CH), 5.83 (s, 1H, C-2 CH), 6.74 (s, 2H, ArH), 6.90 (d, 1H, ArH), 7.59 (d, 2H, ArH), 8.02 (d, 1H, ArH), 8.13 (s, 2H, ArH).

Preparation of Trans-2-[4-allyloxy-5-{N-(m-morpholinomethylbenzoyloxy)-N-methylureidyl}-3 -methoxyphenyl]-4-(3,4,5-trimethoxyphenyl)-1,3-dithiolane (17)

Trans-2-[4-allyloxy-5-{N-(m-chloromethylbenzoyloxy)-N-methylureidyl}-3 -methoxyphenyl]-4-(3,4,5-trimethoxyphenyl)-1,3-dithiolane (15) (0.120 g, 0.177 mmole), sodium iodide (27 mg, 0.177 mmole), morpholine (38 µl, 0.442 mmole), and 10 ml acetone were refluxed for 2 hours under an argon atmosphere. The solvent was removed in vacuo, and the remaining oil was purified by flash column chromatography with 1:1 hexane/ethyl acetate as eluent. (110 mg, 85% yield: clear oil).

Trans epimer: $^1$H NMR (300 MHz, CDCl$_3$) 2.45 (t, 4H, NCH$_2$), 3.44 (s, 3H, CH$_3$), 3.47 (dd, 1H, C-5 CH), 3.57 (s, 2H, CH$_2$N), 3.65 (dd, 1H, C-5 CH), 3.72 (t, 4H, OCH$_2$), 3.85 (s, 3H, OCH$_3$), 3.86 (s, 3H, OCH$_3$), 3.89 (s, 6H, OCH$_3$), 4.34 (d, 2H, OCH$_2$), 4.90 (dd, 2H, CH$_2$=), 5.09 (dd, 1H, C-4 CH), 5.65 (m, 1H, CH=), 5.83 (s, 1H, C-2 CH), 6.74 (s, 2H, ArH), 6.90 (d, 1H, ArH), 7.49 (t, 1H, ArH), 7.68 (dt, 1H, ArH), 7.98 (bs, 1H, ArNHC(O)), 8.06 (dt, 1H, ArH), 8.08 (m, 1H, ArH), 8.16 (d, 1H, ArH).

Preparation of Trans-2-[3,4-dimethoxy-5-{N-(p-morpholinomethylbenzoyl-oxy)-N-methylureidyl} phenyl]-4 -(3,4,5-trimethoxyphenyl)-1,3-dithiolane (18)

Trans-2-[3,4-dimethoxy-5-{N-(p-chloromethylbenzoyl-oxy)-N-methylureidyl}phenyl]-4 -(3,4,5-trimethoxyphenyl)-1,3-dithiolane (16) 0.048 g, 0.074 mmole), sodium iodide (11 mg, 0.074 mmole), morpholine (19 µl, 0.221 mmole), and 10 ml acetone were refluxed for 3 hours under an argon atmosphere. The reaction was 90% complete by TLC so the reaction was cooled to room temperature and stirred overnight. Unfortunately, after stirring overnight, a significant portion of desired product had been saponified back to hydroxyurea 1. The solvent was removed in vacuo, and the remaining oil was purified by flash column chromatography with 1:1 hexane/ethyl acetate as eluent. Both the desired product 18 (4 mg: clear oil) and saponified product 1 (21 mg) were recovered from the column.

Trans epimer: $^1$H NMR (300 MHz, CDCl$_3$) 2.45 (t, 4H, NCH$_2$), 3.45 (s, 3H, NCH$_3$), 3.46 (dd, 1H, C-5 CH), 3.59 (s, 2H, CH$_2$N), 3.65 (dd, 1H, C-5 CH), 3.74 (t, 4H, OCH$_2$), 3.85 (s, 3H, OCH$_3$), 3.88 (s, 3H, OCH$_3$), 3.89 (s, 9H, OCH$_3$), 5.09 (dd, 1H, C-4 CH), 5.83 (s, 1H, C-2 CH), 6.74 (s, 2H, ArH), 6.90 (d, 1H, ArH), 7.54 (d, 2H, ArH), 8.02 (d, 1H, ArH), 8.12 (s, 2H, ArH), 8.14 (bs, 1H, ArNHC(O)).

Preparation of 1-(3,4,5-Trimethoxyphenyl)-1,2-ethanedithiol: (20)

Lithium aluminum hydride (0.20 g, 5.27 mmole) was added to 15 ml dry diethyl ether. To this slurry was added 4-(3,4,5-trimethoxyphenyl)-1,3-dithiolane-2-thione (31) (1.0 g, 3.31 mmole) predissolved in 20 ml dry THF. The reaction was refluxed under an N$_2$ atmosphere for 12 hours. The reaction was cooled to 0° C. and the excess hydride destroyed with H$_2$O. The reaction mixture was acidified with 10% HCl and immediately extracted with diethyl ether. The organic layer was washed with H$_2$O, dried over MgSO$_4$, filtered and evaporated to a white solid (0.836 g, 97%).

NMR: (CDCl$_3$) 2.34, d, 1H; 2.95, m, 1H; 3.09, m, 1H; 3.84, s, 3H; 3.87 , s, 6H; 4.03, m, 1H; 6.53, s, 2H.

M.S. (IBu) 261 (100%). Melting Point: 72.5°–73.5° C.

Anal. calcd. for C$_{11}$H$_{16}$O$_3$S$_2$: C, 50.74; H, 6.19; S, 24.63. Found: C, 50.85; H, 6.20; S, 24.53.

Preparation of 2-(4-Hydroxy-3-nitro-5-methoxyphenyl)-4-(3,4,5-trimethoxyphenyl)-1,3-dithiolane: (21)

1-(3,4,5-Trimethoxyphenyl)-1,2-ethanedithiol (20) (25.4 g, 97.7 mmole), 5-nitrovanillin (16.73 g, 84.9 mmole), PPTS (8.52 g, 33.9 mmole) and 100 ml dry benzene were refluxed under an argon atmosphere with Dean-Stark removal of the benzene-water azeotrope for 12 hours. The reaction was cooled to room temperature and the precipitated PPTS removed by vacuum filtration. Hexane (100 ml) was added to the filtrate and the precipitate collected by vacuum filtration. The yellow solid was washed with cold water, followed by minimal cold methanol and finally cold diethyl ether to leave 28.62 g of a 1:1.3 cis/trans ratio of product. Six recrystallizations from ethyl acetate/hexane gives 4.3 g of pure trans diastereomer. An additional 2.4 g trans product can be obtained by repeating the above crystallization process from the material remaining in the mother liqours. Once 6.7 g of trans product was isolated, 0.315 g of cis diastereomer was isolated by recrystallizing the combined mother liqours from above.

Trans epimer: $^1$H NMR (300 MHz, CDCl$_3$) d 3.50 (dd, 1H, C-5 CH), 3.66 (dd, 1H, C-5 CH), 3.84 (s, 3H, OCH$_3$), 3.88 (s, 6H, OCH$_3$), 4.00 (s, 3H, OCH$_3$), 5.05 (dd, 1H, C-4 CH), 5.80 (s, 1H, C-2 CH), 6.72 (s, 2H, ArH), 7.41 (d, 1H, ArH), 7.90 (d, 1H, ArH). MS (IBu) m/e: 440 (M$^+$); mp: 149°–151° C. (EtOCAc/hexane); Anal. Calcd for C$_{19}$H$_{21}$O$_7$S$_2$N: C, 51.92; H, 4.82; S, 14.59; N, 3.19. Found: C, 52.03; H, 4.86; S, 14.51; N, 3.19.

Cis epimer: $^1$H NMR (300 MHz, CDCl$_3$) d 3.53 (d, 2H, C-5 CH$_2$), 3.84 (s, 3H, OCH$_3$), 3.89 (s, 6H, OCH$_3$), 3.97 (s, 3H, OCH$_3$), 4.88 (t, 1H, C-4 CH), 5.70 (s, 1H, C-2 CH), 6.75 (s, 2H, ArH), 7.37 (d, 1H, ArH), 7.97 (d, 1H, ArH). MS (IBu) m/e: 440 (M$^+$); Mp: 120°–121° C. (EtOAc/hexane); Anal Calcd for C$_{19}$H$_{21}$O$_7$S$_2$N: C, 51.92; H, 4.82. Found: C, 52.05; H, 4.87.

Preparation of Trans and Cis-2-(3,4-dimethoxy-5-nitrophenyl)-4-(3,4,5-trimethoxyphenyl)-1,3-dithiolane (22)

Using the Aldrich diazald kit, diazald (13.0 g, 60.7 mmole) predissolved in 100 ml diethyl ether was added dropwise to an aqueous potassium hydroxide solution (ethanol, 27 ml; $H_2O$, 21 ml; and potassium hydroxide, 13.3 g) at 65° C. The diazomethane/ether distillate was added at 0° C. to a solution of trans-2-(4-hydroxy-3-methoxy-5-nitrophenyl)-4-(3,4,5-trimethoxyphenyl)-1,3-dithiolane (21) predissolved in 25 ml chloroform and 50 ml methanol. The reaction was stirred to completely homogenize the solution and was then allowed to stand at room temperature under an argon atmosphere for 5 hours. The solvent was removed in vacuo and the remaining oil was dissolved in 10 ml diethyl ether. The product crystallized out of the ether solution to yield 3.285 g (98%) of light yellow crystals.

Trans epimer: $^1$H NMR (300 MHz, $CDCl_3$) d 3.49 (dd, 1H, C-5 CH), 3.65 (dd, 1H, C-5 CH), 3.84 (s, 3H, $OCH_3$), 3.88 (s, 6H, $\overline{OCH}_3$), 3.96 (s, 3H, $OCH_3$), 3.97 (s, 3H, $OCH_3$), 5.04 (dd, 1H, C-4 CH), 5.78 (s, 1H, C-2 CH), 6.71 (s, 2H, ArH), 7.32 (d, 1H, ArH), 7.58 (d, 1H, ArH); MS (IBu) m/e: 454 ($M^+$); mp: 133°–134° C. (EtOAc/hexane); Anal Calcd for $C_{20}H_{23}O_7S_2N$: C, 52.97; H, 5.11; S, 14.14; N, 3.09. Found: C, 52.92; H, 5.06; S, 14.06; N, 3.14.

The cis product can be obtained in the same manner as above starting from cis-2-(4-hydroxy-3-methoxy-5-nitrophenyl)-4-(3,4,5-trimethoxyphenyl)-1,3-dithiolane (21).

Cis epimer: $^1$H NMR (300 MHz, $CDCl_3$) d 3.55 (d, 2H, C-5 $CH_2$), 3.84 (s, 3H, $OCH_3$), 3.88 (s, 6H, $OCH_3$), 3.93 (s, 3H, $OCH_3$), 3.97 (s, 3H, $OCH_3$) 4.88 (t, 1H, C-4 CH), 5.70 (s, 1H, C-2 CH), 6.73 (s, 2H, ArH), 7.30 (d, 1H, ArH), 7.65 (d, 1H, ArH) MS (IBu) m/e: 454 ($M^+$); mp: 99°–100° C. ($Et_2O$); Anal Calcd for $C_{20}H_{23}O_7S_2N$: C, 52.97; H, 5.11; S, 14.14; N, 3.09. Found: C, 53.08; H, 5.09; S, 14.04; N, 3.10.

Preparation of Trans and Cis-2-(5-amino-3,4-dimethoxyphenyl)-4-(3,4,5-trimethoxy-phenyl)-1,3-dithiolane (23)

Trans-2-(3,4-dimethoxy-5-nitrophenyl)-4-(3,4,5-trimethoxyphenyl)-1,3-dithiolane (22) (3.10 g, 6.84 mmole) was predissolved in 33 ml absolute ethanol. To this solution was added calcium chloride (0.721 g, 6.50 mmole) predissolved in 7 ml $H_2O$ followed by freshly activated zinc dust (10.0 g, 195 mmole). The reaction was refluxed for 12 hours. The solid was removed by vacuum filtration through celite and was washed with ethyl acetate. The filtrate was washed with $H_2O$, dried over $MgSO_4$, and evaporated in vacuo to a white foam (2.52 g, 87%).

Trans epimer: $^1$NMR (300 MHz, $CDCl_3$) d 3.45 (dd, 1H, C-5 CH), 3.63 (dd, 1H, C-5 CH), 3.81 (s, 3H, $OCH_3$) 3.84 (s, 6H, $\overline{OCH}_3$), 3.87 (s, 3H, $OCH_3$), 3.88 (s, 3H, $OCH_3$), 5.04 (dd, 1H, C-4 CH), 5.75 (s, 1H, C-2 CH); 6.56 (d, 1H, ArH), 6.65 (d, 1H, ArH), 6.72 (s, 2H, ArH); MS (IBu) m/e: 424 ($M^+$), 227, 195; mp: 48°–51° C. (foam); Anal Calcd for $C_{20}H_{25}O_5S_2N$: C, 56.72; H, 5.95; S, 15.14; N, 3.31. Found: C, 56.79; H, 5.96; S, 15.04; N, 3.35.

The cis product can be obtained in the same manner as above starting from cis-2-(3,4-dimethoxy-5-nitrophenyl)-4-(3,4,5-trimethoxyphenyl)-1,3-dithiolane (22).

Cis epimer: $^1$H NMR (300 MHz, $CDCl_3$) d 3.53 (d, 2H, C-5 $CH_2$), 3.81 (s, 3H, $OCH_3$), 3.83 (s, 6H, $OCH_3$), 3.85 (s, 3H, $OCH_3$), 3.87 (s, 3H, $OCH_3$) 4.81 (t, 1H, C-4 CH), 5.68 (s, 1H, C-2 CH), 6.64 (d, 1H, Ar-H), 6.68 (d, 1H, ArH) 6.74 (s, 2H, ArH);

MS (CI) m/e: 4.24 ($M^+$) 227, 195.

Preparation of Trans-2-(4-allyloxy-3-methoxy-5-nitrophenyl)-4-(3,4,5-trimethoxyphenyl)-1,3-dithiolane (24)

Trans-2-(4-hydroxy-3-methoxy-5-nitrophenyl)-4-(3,4,5-trimethoxy-phenyl)-1,3-dithiolane (21) (2.50 g, 5.69 mmole) was dissolved in 30 ml dry DMF and allyl bromide (0.963 g, 7.97 mmole) was added by syringe. To this solution was added 100 mg of 18-crown-6 and potassium carbonate (0.785 g, 5.69 mmole). The reaction was stirred at 50° C. under an argon atmosphere for 4 hours. The reaction was quenched with 10% HCl and extracted with diethyl ether. The organic layer was dried over $MgSO_4$, and concentrated to a yellow oil in vacuo which was purified by flash column chromatography with 3:1–2:1 hexane/ethyl acetate as eluent. (2.60 g, 95% yield: colorless oil).

Trans epimer: $^1$H NMR (300 MHz, $CDCl_3$) d 3.50 (dd, 1H, C-5 CH), 3.65 (dd, 1H, C-5 CH), 3.85 (s, 3H, $OCH_3$), 3.89 (s, 6H, $\overline{OCH}_3$), 3.95 (s, 3H, $OCH_3$), 4.65 (d, 2H, $OCH_2$), 5.04 (dd, 1H, C-4 CH), 5.31 (dd, 2H, $=CH_2$), 5.79 (s, 1H, C-2 CH), 6.08 (m, 1H, CH=), 6.72 (s, 2H, ArH), 7.32 (d, 1H, ArH), 7.58 (d, 1H, ArH).

Preparation of Trans-2-(4-allyloxy-5-amino-3-methoxyphenyl)-4-(3,4,5-trimeth-oxyphenyl)-1,3-dithiolane (25)

Trans-2-(4-allyloxy-3-methoxy-5-nitrophenyl)-4-(3,4,5-trimethoxy-phenyl)-1,3-dithiolane (24) 2.60 g, 5.43 mmole) was predissolved in 33 ml absolute ethanol. To this solution was added calcium chloride (0.602 g, 5.43 mmole) predissolved in 7 ml $H_2O$ followed by freshly activated zinc dust (7.09 g, 108 mmole). The reaction was refluxed for 12 hours. The solid was removed by vacuum filtration through celite and was washed with ethyl acetate. The filtrate was washed with 10% $NaHCO_3$, dried over $MgSO_4$, and

Preparation of Trans-2-(4-(2-methanesulfonyloxyethoxy)-3-methoxy-5-nitrophenyl)-4-(3,4,5-trimethoxyphenyl)-1,3-dithiolane (28)

Trans-2-(4-(2-hydroxyethoxy-3-methoxy-5-nitrophenyl)-4-(3,4,5-trimethoxyphenyl)-1,3-dithiolane (27) (0.600 g, 1.24 mmole) was dissolved in 15 ml dry dichloromethane and triethylamine (0.376 g, 3.72 mmole) was added by syringe. To this solution was added 144 μl of methane sulfonyl chloride. The reaction was stirred at room temperature under an argon atmosphere for 5 hours. The reaction was quenched with 15 ml 10% NaOH and extracted with additional dichloromethane. The organic layer was dried over $MgSO_4$, and concentrated to an oil in vacuo which was purified by flash column chromatography with 1:1 hexane/ethyl acetate as eluent. (0.650 g, 93% yield: colorless oil).

Preparation of Trans-2-[4-{2-(4'-bromophenylthio)ethoxy}-3-methoxy-5-nitrophenyl]-4-(3,4,5-trimethoxyphenyl)-1,3-dithiolane (29, CMI-03-296DG)

Trans-2-[4-(2-(methanesulfonyloxy)ethoxy}-3-methoxy-5-nitrophenyl]-4-(3,4,5-trimethoxyphenyl)-1,3-dithiolane (28) (0.640 g, 1.14 mmole), 4-bromothiophenol (0.646 g, 3.42 mmole), triethylamine (0.346 g, 3.42 mmole) and 20 ml ethanol was refluxed for 24 hours under an argon atmosphere. The product was extracted into ethyl acetate, washed with 10% $K_2CO_3$, dried over $MgSO_4$, and concentrated to a yellow foam in vacuo which was purified by flash column chromatography with 2:1 hexane/ethyl acetate as eluent. (484 mg, 65% yield: foam).

Trans epimer: $^1$H NMR (300 MHz, $CDCl_3$) 3.31 (t, 2H, $SCH_2$), 3.49 (dd, 1H, C-5 CH), 3.65 (dd, 1H, C-5 CH), 3.85 (s, 3H, $OCH_3$), 3.88 (s, 6H, $OCH_3$), 3.90 (s, 3H, $OCH_3$), 4.26 (t, 2H, $OCH_2$), 5.04 (dd, 1H, C-4 CH), 5.78 (s, 1H, C-2 CH), 6.71 (s, 2H, ArH), 7.25 (d, 2H, ArH), 7.30 (d, 1H, ArH), 7.42 (d, 2H, ArH), 7.58 (d, 1H, ArH).

Preparation of 1-(3,4,5-Trimethoxyphenyl)oxirane: (30)

3,4,5-Trimethoxy-benzaldehyde (9.80 g, 50.0 mmole) was dissolved in 20 ml $CH_2Cl_2$ along with tetrabutylammonium iodide (0.396 g, 1.00 mmole). To this solution was added a cooled 50% NaOH solution (10 g NaOH in 10 ml $H_2O$). To this mixture was added trimethylsulfonium iodide (10.20 g, 50.0 mmole). The reaction was refluxed with vigorous stirring for 15 hours. The reaction was queched with $H_2O$, extracted with $CH_2Cl_2$, washed with brine, dried over $MgSO_4$ and evaporated to an oil (9.69 g, 84%) which solidified to a white solid after 24 hours in vacuo.

NMR: ($CDCl_3$) 2.75, dd, 1H; 3.11, dd, 1H; 3.81, d, 1H; 3.82, s, 3H; 3.85 , s, 6H; 6.50, s, 2H

M.S. (CI): 211 (100%). Melting Point: 54.5°–56° C.

Anal. calcd. for $C_{11}H_{14}O_4$: C, 62.85; H, 6.71. Found: C, 62.63; H, 6.76.

Preparation of 4-(3,4,5-Trimethoxyphenyl)-1,3-dithiolane-2-thione: (31)

Powdered potassium hydroxide (2.40 g, 42.85 mmole) was dissolved in 10.0 ml methanol and carbon disulfide (3.10 ml, 51.43 mmole) was added at 0° C. under an $N_2$ atmosphere. The reaction mixture was shaken vigorously and 1-(3,4,5-trimethoxyphenyl)oxirane (30) (3.50 g, 16.66 mmole) was added. The reaction was allowed to warm to room temperature at which point the reaction started to reflux for twenty minutes. Subsequently, the reaction was stirred at room temperature overnight. The yellow precipitate was isolated by suction filtration and was washed with $H_2O$ and diethylether to yield 3.82 g (76%).

NMR: ($CDCl_3$) 3.85, s, 3H; 3.88, s, 6H; 3.99, dd, 1H; 4.17, t, 1H; 5.57 , dd, 1H; 6.70, s, 2H.

M.S.: (IBu) 303 (100%). Melting Point: 152°–154° C.

Anal. calcd. for $C_{12}H_{14}O_3S_3$: C, 47.66; H, 4.67; S, 31.80. Found: C, 47.90; H, 4.70; S, 31.71. evaporated in vacuo to a white foam (1.02 g, 42%). A major second product (cyclic morpholine formed from addition of the aniline to the C-2 of the allyloxy moiety) which had a lower Rf on TLC was formed in 46% yield (1.12 g).

Trans epimer: $^1$H NMR (300 MHz, $CDCl_3$) 3.45 (dd, 1H, C-5 CH), 3.63 (dd, 1H, C-5 CH), 3.84 (s, 6H, $OCH_3$), 3.88 (s, 6H, $OCH_3$), 4.49 (d, 2H, $OCH_2$), 5.04 (dd, 1H, C-4 CH), 5.29 (dd, 2H, =$CH_2$), 5.75 (s, 1H, C-2 CH), 6.05 (m, 1H, CH=), 6.56 (d, 1H, ArH), 6.66 (d, 1H, ArH), 6.73 (s, 2H, ArH).

Side product: $^1$H NMR (300 MHz, $CDCl_3$) 1.18 (d, 3H, $CH_3$), 3.45 (dd, 1H, C-5 CH), 3.63 (dd, 1H, C-5 CH), 3.53 (m, 1H, NCH), 3.80 (dd, 1H, $OCH_2$), 3.84 (s, 3H, $OCH_3$), 3.88 (s, 6H, $OCH_3$), 3.89 (s, 3H, $OCH_3$), 4.28 (dd, 1H, $OCH_2$), 5.04 (dd, 1H, C-4 CH), 5.77 (s, 1H, C-2 CH), 6.72 (m, 4H, ArH).

Preparation of Trans-2-(4-(2-hydroxyethoxy)-3-methoxy-5-nitrophenyl)-4 -(3,4,5-trimethoxyphenyl)-1,3-dithiolane (27)

Trans-2-(4-hydroxy-3-methoxy-5-nitrophenyl)-4-(3,4,5-trimethoxy-phenyl)-1,3-dithiolane (21) (1.00 g, 2.27 mmole) was dissolved in 45 ml dry DMF and 2-iodoethanol (0.783 g, 4.55 mmole) was added by syringe. To this solution was added 50 mg of 18-crown-6 and potassium carbonate (0.344 g, 2.49 mmole). The reaction was stirred at 80° C. under an argon atmosphere for 3 days. An additional 200 mg of 2-iodoethanol was added and after 3 additional hours, the reaction was complete. The reaction was quenched with 10% HCl and extracted with ethyl acetate. The organic layer was dried over $MgSO_4$, and concentrated to an oil in vacuo which was purified by flash column chromatography with 2:1 hexane/ethyl acetate as eluent. (1.01 g, 92% yield: colorless oil).

Trans epimer: $^1$H NMR (300 MHz, $CDCl_3$) d 3.51 (dd, 1H, C-5 CH), 3.65 (dd, 1H, C-5 CH), 3.86 (s, 3H, $OCH_3$), 3.90 (s, 6H, $OCH_3$), 3.93 (t, 2H, $CH_2OH$), 3.96 (s, 3H, $OCH_3$), 4.33 (t, 2H, $OCH_2$), 5.04 (dd, 1H, C-4 CH), 5.80 (s, 1H, C-2 CH), 6.73 (s, 2H, ArH), 7.36 (d, 1H, ArH), 7.66 (d, 1H, ArH).

Scheme 1:

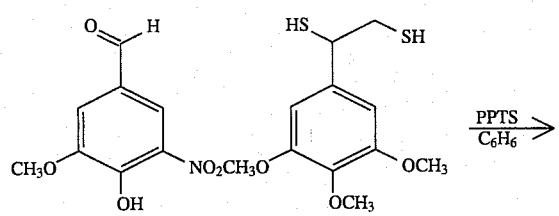

Scheme 1:
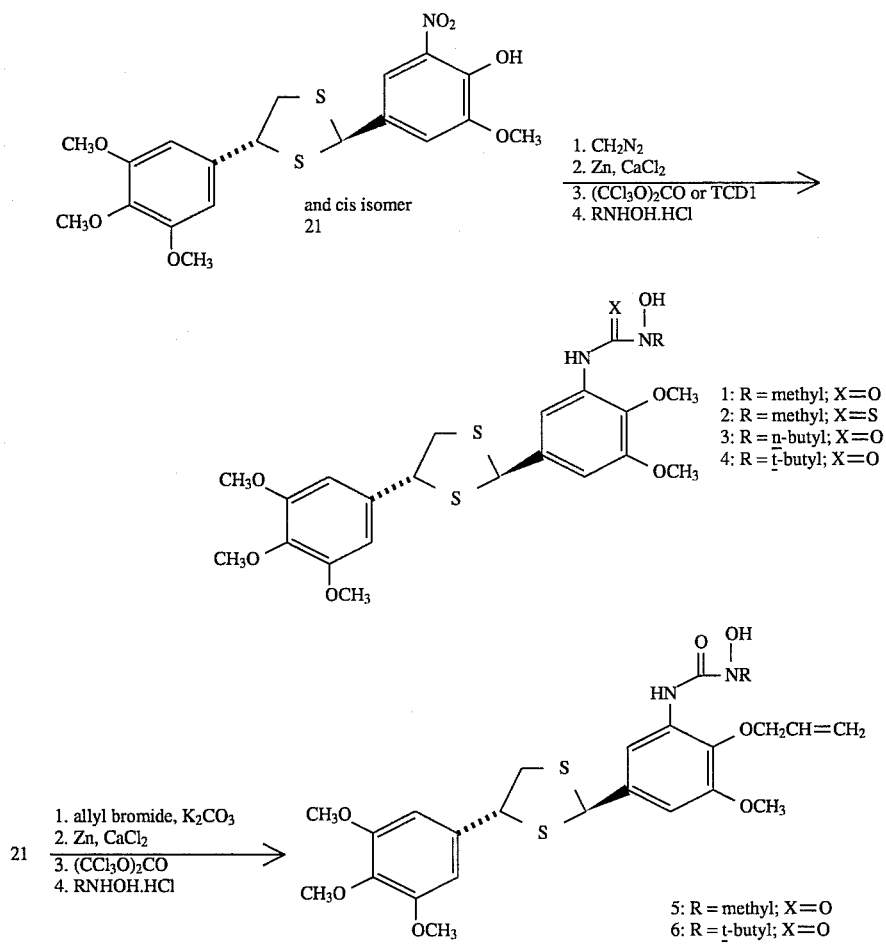
Scheme 2:
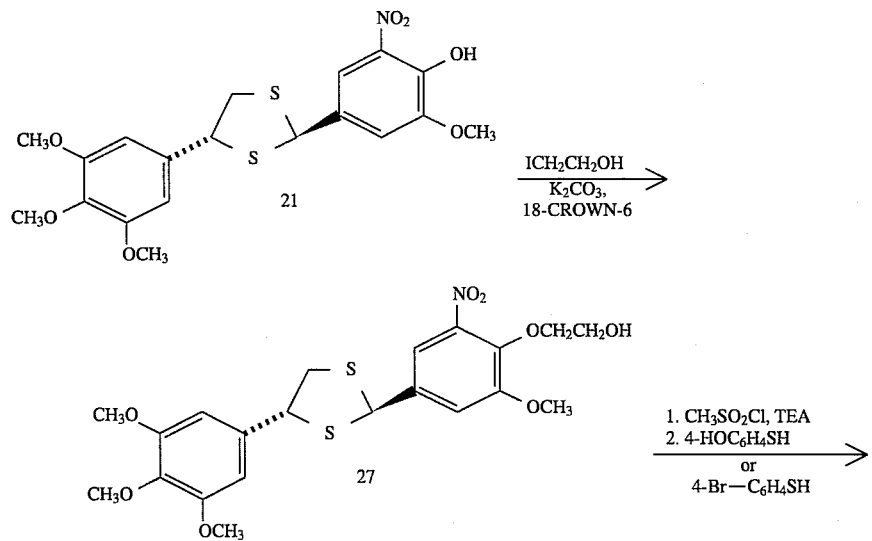

Scheme 2:
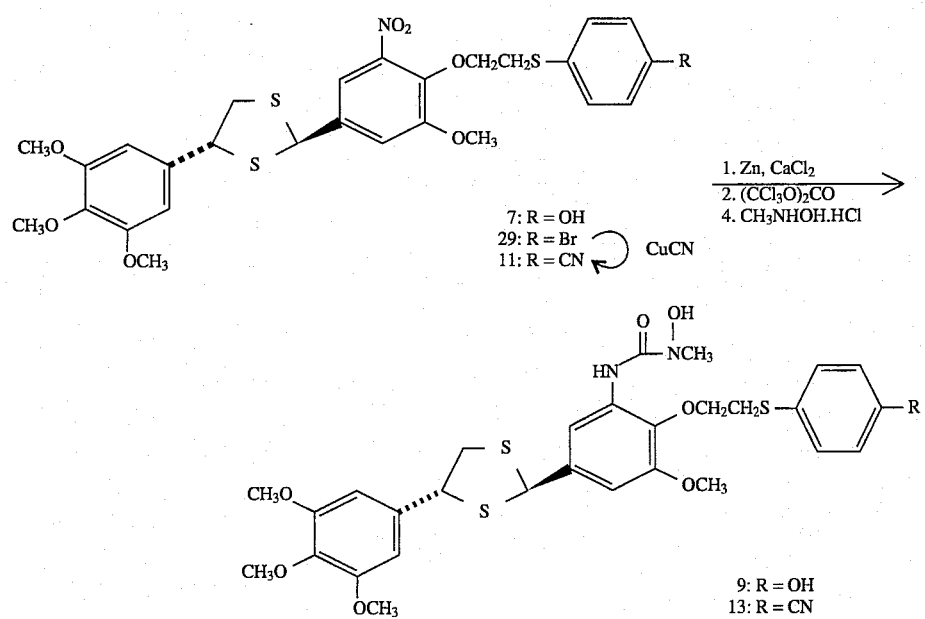
Scheme 3:
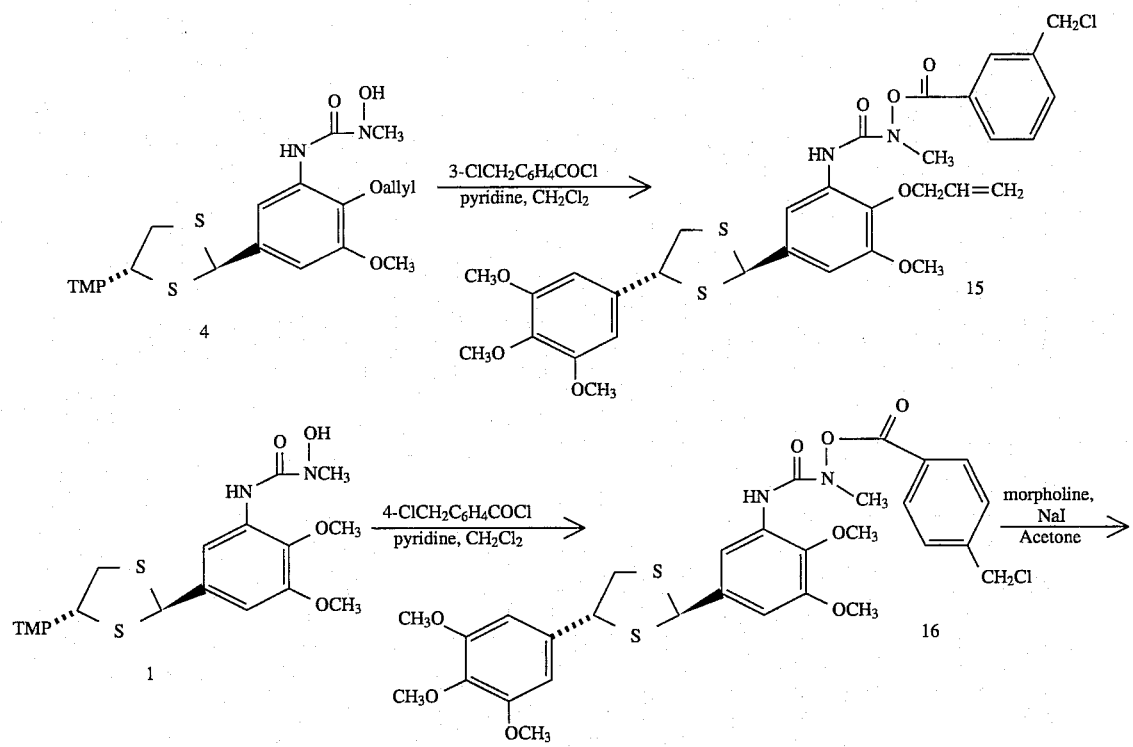

-continued
Scheme 3:
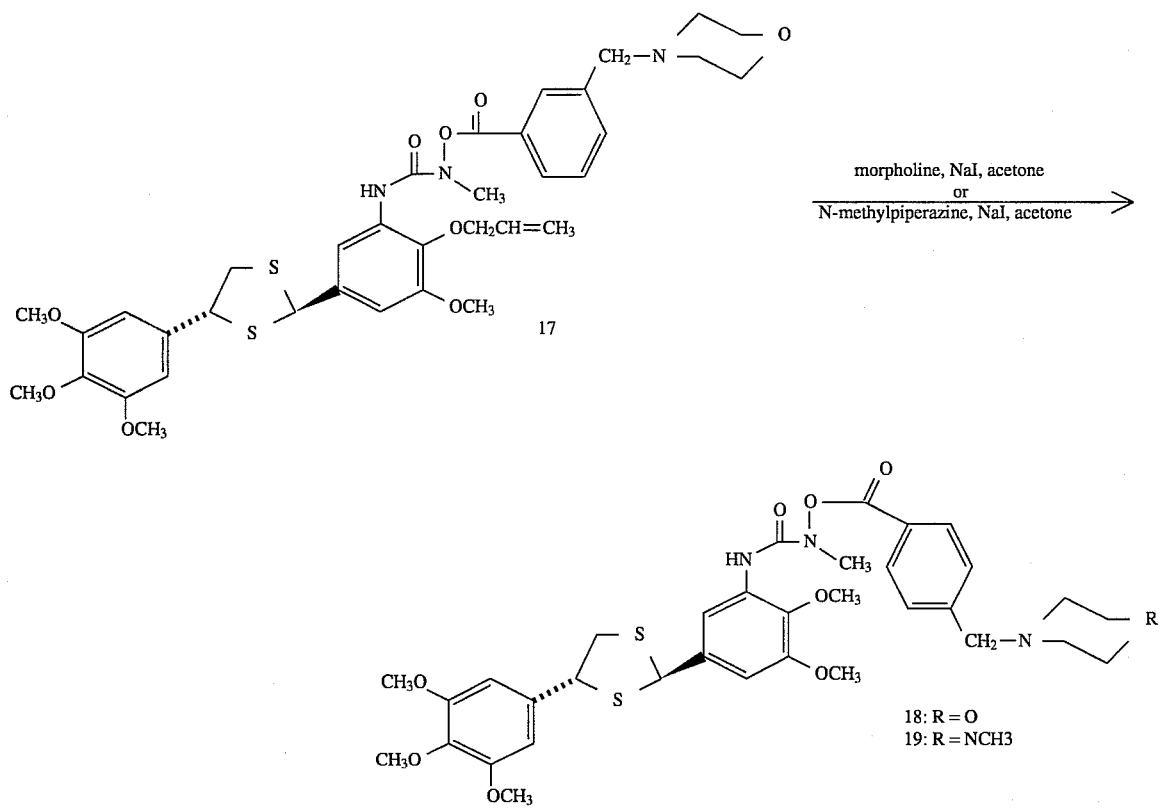
Scheme 4:
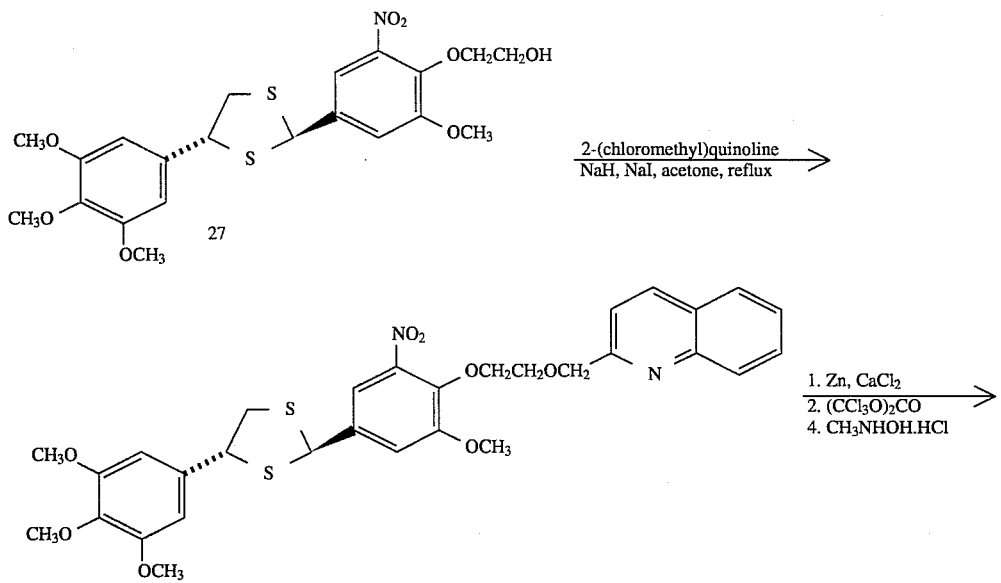

-continued
Scheme 4:
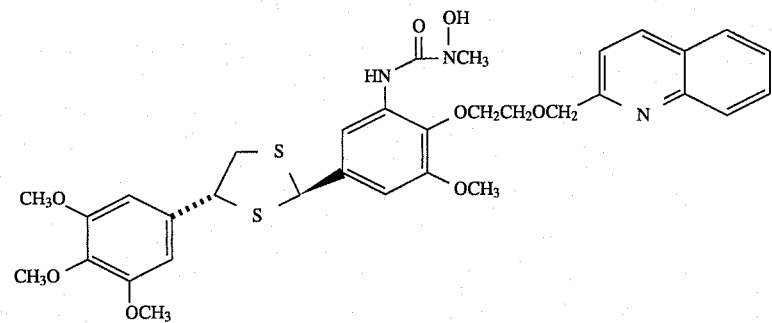
Scheme 5:
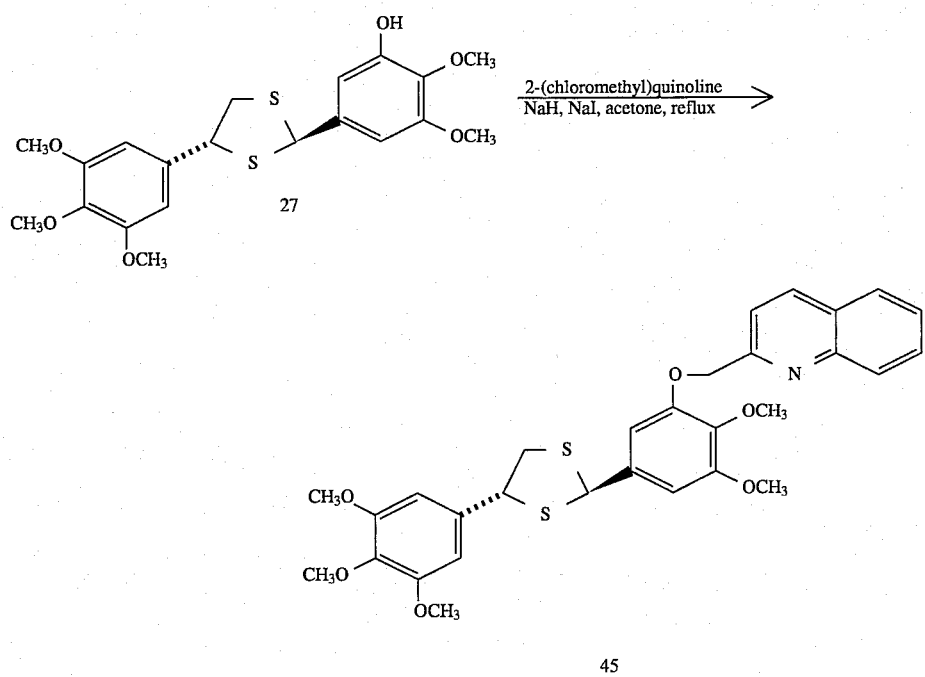

Scheme 6:
The Preparation of Oxothiolane derivatives for the optically active isomers
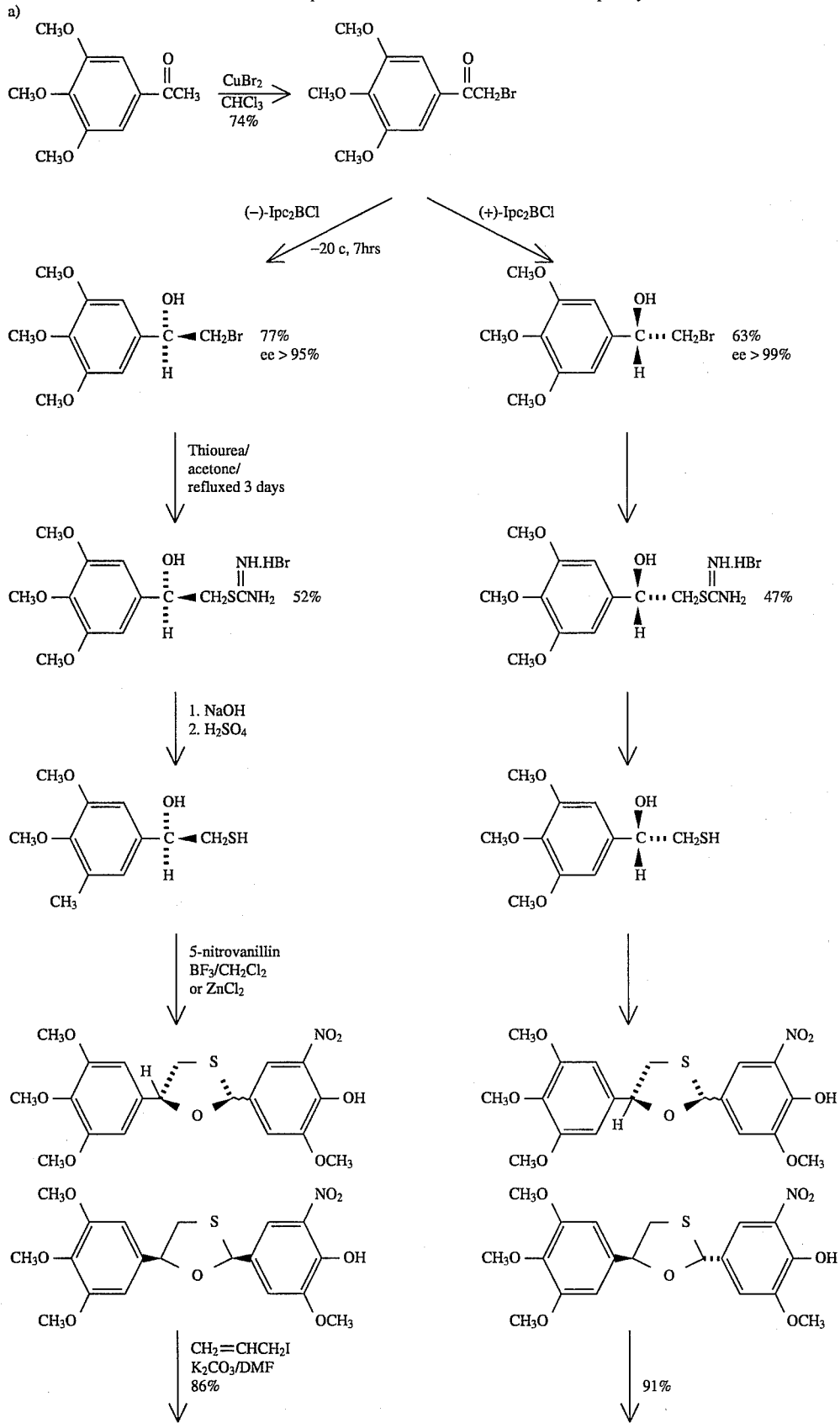

Scheme 6:

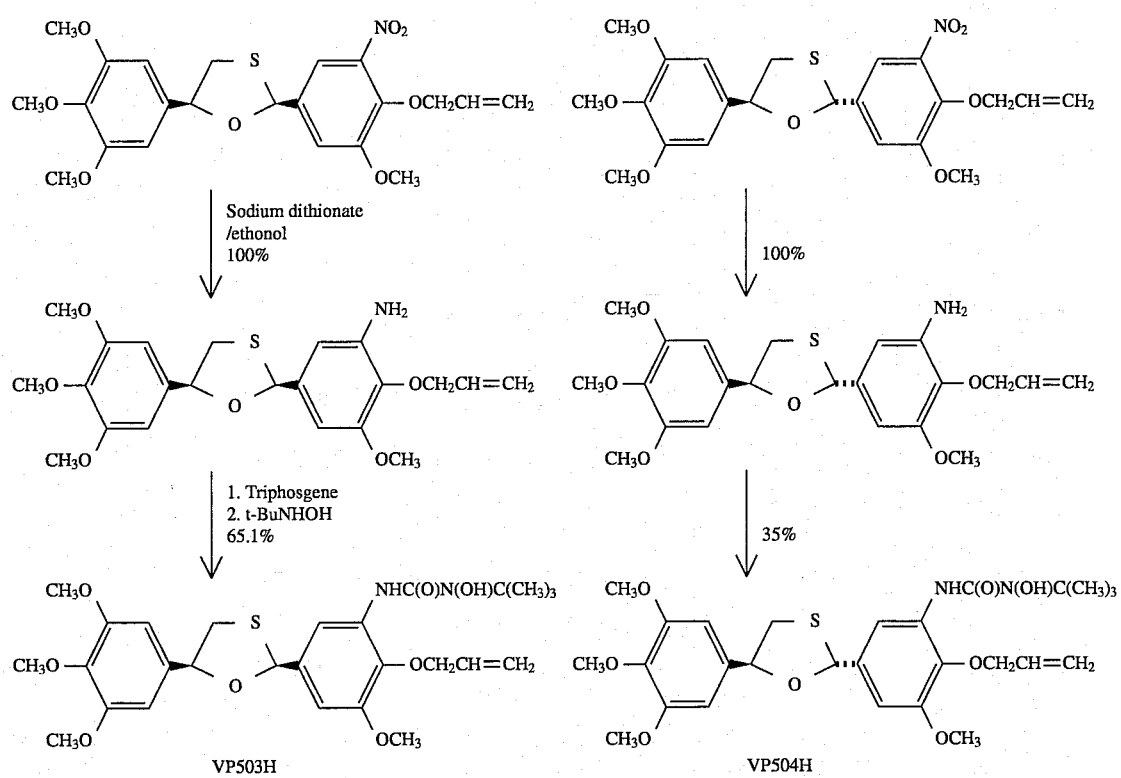

II. Pharmaceutical Compositions

Humans, equine, canine, bovine and other animals, and in particular, mammals, suffering from disorders mediated by PAF or products of 5-lipoxygenase can be treated by administering to the patient an effective amount of one or more of the above-identified compounds or a pharmaceutically acceptable derivative or salt thereof in a pharmaceutically acceptable carrier or diluent. The active materials can be administered by any appropriate route, for example, orally, parenterally, intravenously, intradermally, subcutaneously, or topically, in liquid, cream, gel or solid form.

As used herein, the term pharmaceutically acceptable salts or complexes refers to salts or complexes that retain the desired biological activity of the above-identified compounds and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01–3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The compound is conveniently administered in any suitable unit dosage form, including but not limited to one containing 1 to 3000 mg, preferably 5 to 500 mg of active ingredient per unit dosage form. A oral dosage of 25–250 mg is usually convenient.

The active ingredient should be administered to achieve peak plasma concentrations of the active compound of about 0.01–30 mM, preferably about 0.1–10 mM. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivatives or salts thereof can also be mixed with other active materials that do not impair the desired action, or with materials that supplement the desired action, such as antibiotics, antifungals, antiinflammatories, or antiviral compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

III. Biological Activity

A wide variety of biological assays have been used to evaluate the ability of a compound to act as a PAF receptor antagonist, including the ability of the compound to bind to PAF receptors, and the effect of the compound on various PAF mediated pathways. Any of these known assays can be used to evaluate the ability of the compounds disclosed herein to act as PAF receptor antagonists.

For example, PAF is known to induce hemoconcentration and increased permeability of microcirculation leading to a decrease in plasma volume. PAF mediated acute circulatory collapse can be used as the basis of an assay to evaluate the ability of a compound to act as a PAF antagonist, by analyzing the effect of the compound on PAF induced decreased plasma volume in an animal model such as mouse.

Endotoxemia causes the release of chemical mediators including eicosanoids, PAF, and tumor necrosis factor (TNF) that stimulate a variety of physiologic responses including fever, hypotension, leukocytosis, and disturbances in glucose and lipid metabolism. Endotoxemia can result in severe shock and death. Endotoxin-induced mouse mortality is a useful animal model to evaluate the pharmacological effect of compounds on endotoxic shock.

Two other common assays used to evaluate the ability of a compound to act as a PAF receptor antagonist are platelet aggregation in vitro and hypotension in rats (Shen, et al., "The Chemical and Biological Properties of PAF Agonists, Antagonists, and Biosynthetic Inhibitors", *Platelet-Activating Factor and Related Lipid Mediators*, F. Snyder, Ed. Plenum Press, New York, N.Y. 153 (1987).)

A wide variety of biological assays have also been used to evaluate the ability of a compound to inhibit the enzyme 5-lipoxygenase. For example, a cytosol 5-lipoxygenase of rat basophilic leukemia cells (RBL) has been widely utilized in studies on leukotriene biosynthesis. Compounds that inhibit 5-lipoxygenase decrease the levels of leukotrienes.

Another biological assay used to evaluate the ability of a compound to inhibit the enzyme 5-lipoxygenase is based on the classic pharmacological model of inflammation induced by the topical application of arachidonic acid to the mouse ear. On application, arachidonic acid is converted by 5-lipoxygenase to various leukotrienes (and other mediators), which induce changes in blood flow, erythema, and increase vasodilation and vasopermeability. The resulting edema is measured by comparing the thickness of the treated ear to a control ear. Agents that inhibit 5-lipoxygenase reduce the edematous response, by lowering the amounts of biochemical mediators formed from arachidonic acid.

Selected 2,4-diaryl-1,3-dithiolanes and 2,5-diaryl-1,3-oxathiolanes disclosed herein were evaluated for biological activity, as described in detail below.

EXAMPLE 2

Ability of Compound to Bind to PAF Receptors a) Preparation of Human Platelet Membranes:

Human platelet membranes were prepared from platelet concentrates obtained from the American Red Cross Blood Services (Dedham, Mass.). After several washes with platelet wash solution (150 mM NaCl, 10 mM Tris, and 2 mM EDTA, pH 7.5), the platelet pellets were resuspended in 5 mM $MgCl_2$, 10 mM Tris, and 2 mM EDTA at pH 7.0. The cells were then quickly frozen with liquid nitrogen and thawed slowly at room temperature. The freezing and thawing procedure was repeated at least three times. For further fractionation of membrane fragments, the lysed membrane suspension was layered over the top of a discontinous sucrose density gradient of 0.25, 1.03, and 1.5M sucrose prepared in 10 mM $MgCl_2$, 10 mM Tris and 2 mM EDTA, pH 7.0, and centrifuged at 63,500×g for 2 hr. The membrane fractions banding between 0.25 and 1.03M (membrane A) and between 1.03 and 1.5M (membrane B) were collected separately. The protein concentration of the membrane preparations was determined by Lowry's method with bovine serum albumin (BSA) as the standard. The membranes were then separated into smaller fractions (4 ml each) and stored at −80° C. and thawed before use.

b) [$^3$H]PAF Binding inhibition:

The ability of [$^3$H]PAF to bind to specific receptors on human platelet membranes was evaluated at optimal conditions at pH 7.0 and in the presence of 10 mM $MgCl_2$. Membrane protein (100 ug) was added to a final 0.5 ml solution containing 0.15 pmol (0.3 nM concentration) of [$^3$H]PAF and a known amount of unlabeled PAF or PAF receptor antagonist in 10 mM $MgCl_2$, 10 mM Tris and 0.25% BSA at pH 7.0. After incubation for four hours at 0° C., the bound and unbound [$^3$H]PAF were then separated through a Whatman GF/C glass fiber filter under vacuum. No degradation of filter bound [$^3$H]PAF has been detected under this assay condition. The nonspecific binding was defined as the total binding in the presence of excess unlabeled PAF (1 mM) where no further displacement was found with higher concentrations of either unlabeled PAF or PAF analogs or PAF receptor antagonists. The specific binding was defined as the difference between total binding and nonspecific binding.

To determine the relative potency of tested compounds, [$^3$H]PAF binding in the presence of inhibitors was normalized in terms of percent inhibition by assigning the total binding in the absence of inhibitors as 0% inhibition and the total binding in the presence of 1 mM unlabeled PAF as 100%. The percent inhibition by the compound can be calculated by the formula expressed below:

% inhibition=[(Total binding−total binding in the presence of compound)/nonspecific binding]×100%

The $IC_{50}$ was calculated as the concentration of the inhibitor necessary to obtain 50% inhibition of the specific [$^3$H]PAF binding and was calculated by a nonlinear regression computer software program, GraphPad Inplot, version 3.0 (GraphPad software, San Diego, Calif.). Table 1 provides the $IC_{50}$ values for a number of 2,4-diaryl-1,3-dithiolanes.

TABLE 1

In-vitro potencies of hydroxyurea 2,4-diaryldithiolane

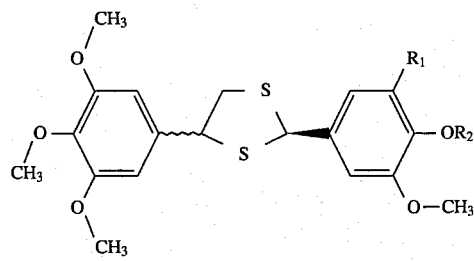

| No. | Isomer | R1 | R2 | PAF (nM) | $IC_{50}$ 5-LO (µM) |
|---|---|---|---|---|---|
| 1. | trans | $NHCONOHCH_3$ | $CH_3$ | 258.6 | 0.22 |
| 2. | trans | $NHCSNOHCH_3$ | $CH_3$ |  | 0.28 |
| 3. | trans | $NHCONOHC_4H_9$ | $CH_3$ | 67.8 | 0.24 |
| 4. | trans | $NHCONOHC(CH_3)_3$ | $CH_3$ | 797.7 | 0.32 |
| 5. | trans | $NHCONOHCH_3$ | $CH_2CH=CH_2$ | 561.0 | 0.17 |
| 6. | trans | $NHCONOHC(CH_3)_3$ | $CH_2CH=CH_2$ | 542.7 | 0.57 |
| 7. | trans | $NO_2$ | $CH_2CH_2SC_6H_4OH$ |  | 57% @ 3 µM |
| 8. | trans | $NH_2$ | $CH_2CH_2SC_6H_4OH$ |  | 41% @ 3 µM |
| 9. | trans | $NHCONOHCH_3$ | $CH_2CH_2SC_6H_4OH$ |  | 0.12 |
| 10. | trans | $NHCONOHC_6H_4Cl$ | $CH_2CH_2SC_6H_4OH$ |  | 64% @ 3 µM |
| 11. | trans | $NO_2$ | $CH_2CH_2SC_6H_4CN$ |  | 20.56 @ 3 µM |
| 12. | trans | $NH_2$ | $CH_2CH_2SC_6H_4CN$ |  | 16.07 @ 3 µM |
| 13. | trans | $NHCONOHCH_3$ | $CH_2CH_2SC_6H_4CN$ |  | 0.092 |
| 14. | trans | $N(CH_3)_2$ | $CH_2CH_2SC_6H_4OH$ |  | 25% @ 3 µM |
| 15. | trans | $NO_2$ | $CH_2CH_2SC_6H_4Br$ |  |  |
| 17. | trans | $NHCONOM^1CH_3$ | $CH_2CH=CH_2$ |  |  |

TABLE 1-continued

In-vitro potencies of hydroxyurea 2,4-diaryldithiolane

| No. | Isomer | R1 | R2 | PAF (nM) | IC$_{50}$ 5-LO (μM) |
|---|---|---|---|---|---|
| 18. | trans | NHCONOM$^2$CH$_3$ | CH$_3$ | | |

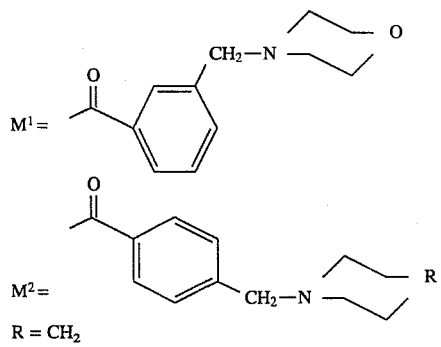

$M^2 =$ $R = CH_2$

EXAMPLE 3

Ability of 2,4-Diaryl-1,3-Dithiolanes and 2,5-Diaryl-1,3-Oxathiolanes to Inhibit Platelet Aggregation The ability of 2,4-diaryl-1,3-dithiolanes and 2,5-diaryl-1,3-oxathiolanes to inhibit platelet aggregation was measured using a method similar to that published by Shen, et al. PAF and Related Lipid Mediators, Plenum Publishers: New York, 1987, 153–190. The results are provided in Table 2.

TABLE 2

The Results of Platelet Aggregation Assay of Several Compounds

| Structure Formula | IC$_{50}$ | RBL 5-LO IC$_{50}$ |
|---|---|---|
| | 63 um | 1.44 |
| | 25 um | 0.85 |

TABLE 2-continued

The Results of Platelet Aggregation Assay of Several Compounds

| Structure Formula | IC$_{50}$ | RBL 5-LO IC$_{50}$ |
|---|---|---|
| 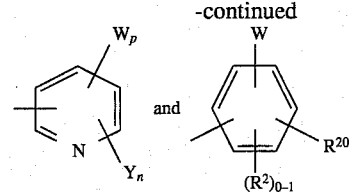 | 53 um | 0.25 |
| 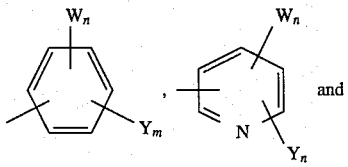 | 10 um | .41 |
| 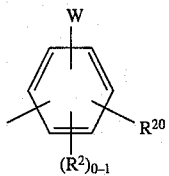 | 141 um | 0 |
| 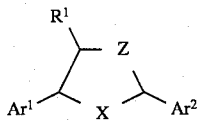 | 30–50 um | 0 |

Modifications and variations of the present invention relating to compounds that reduce the chemotaxis and respiratory burst leading to the formation of damaging oxygen radicals of PMNs during an inflammatory or immune response will be obvious to those skilled in the art from the foregoing detailed description of the invention. Such modifications and variations are intended to come within the scope of the appended claims.

We claim:

1. A compound of formula:

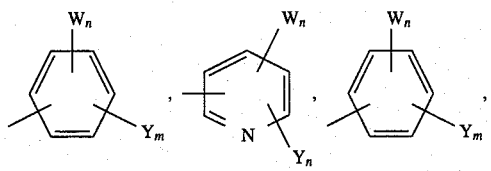

wherein:

Ar$^1$ and Ar$^2$ are independently selected from the group consisting of and wherein at least one of Ar$^1$ and Ar$^2$ is:

X and Z are S;

Q is selected from the group consisting of hydrogen, —AH, —OH, —CN and —R$^{20}$;

W is independently selected from the group consisting of —AN(OM)C(O)N(R$^3$)R$^4$, —AN(R$^3$)C(O)N(OM)R$^4$, —AN(OM)C(O)R$^4$, —AC(O)N(OM)R$^4$,
—N(OM)C(O)N(R$^3$)R$^4$, —N(R$^3$)C(O)N(OM)R$^4$,
—N(OM)C(O)R$^4$, —C(O)N(OM)R$^4$,
—OR$^6$N(R$^5$)R$^6$—(C$_5$H$_4$N)R$^6$R$^7$, —OR$^6$N(COR$^5$)R$^6$—(C$_5$H$_4$N)R$^6$R$^7$, —OR$^6$OC(O)N(COR$^5$)R$^6$—(C$_5$H$_4$N)R$^6$R$^7$, —OR$^6$O(CO)N(CO$_2$R$^6$)R$^6$(C$_5$H$_4$N)R$^6$R$^7$,
—A(C$_5$H$_4$N)R$^6$R$^7$, —OR$^6$N(CO$_2$R$^5$)R$^6$—(C$_5$H$_4$N)R$^6$R$^7$,
—N(R$^{19}$)C(O)C(R$^{19}$)N(OM)C(O)NHR$^{20}$,
—C(O)N(R$^{19}$)C(R$^{19}$)N(OM)C(O)NHR$^{20}$,
—AN(R$^{19}$)C(O)C(R$^{19}$)N(OM)C(O)NHR$^{20}$,
—AC(O)N(R$^{19}$)C(R$^{19}$)N(OM)C(O)NHR$^{20}$,
—NHC(O)N(OM)C(R$^{19}$)C(O)N(R$^{19}$)$_2$,
—NHC(O)N(OM)C(R$^{19}$)N(R$^{19}$)C(O)R$^{19}$;

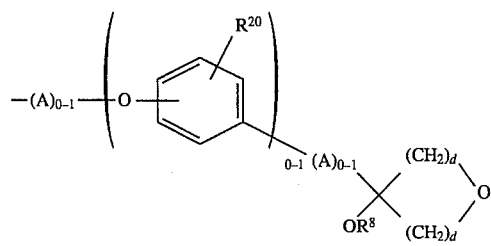

wherein d is independently 1–4;

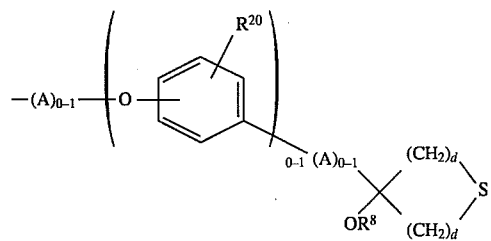

wherein n is 1 or 2; m is 1, 2 or 3; and p is 0 or 1; and wherein A is selected from the group consisting of alkyl, alkenyl, alkynyl, alkaryl, aralkyl, halo lower alkyl, halo lower alkenyl, halo lower alkynyl, —C$_{1-10}$alkyl(oxy)C$_{1-10}$alkyl, —C$_{1-10}$alkyl(thio)C$_{1-10}$alkyl, —N(R$^3$)C(O)alkyl, —N(R$^3$)C(O)alkenyl, —N(R$^3$)C(O)alkynyl, —N(R$^3$)C(O)-(alkyl)oxy(alkyl), —N(R$^3$)C(O)(alkyl)thio(alkyl), —N(R$^3$)C(O)—N-(alkyl), —N(R$^3$)C(O)N(alkenyl), —N(R$^3$)C(O)N(alkynyl), —N(R$^3$)C(O)N(alkyl)oxy(alkyl), —N(R$^3$)C(O)N(alkyl)thio(alkyl), —N(R$^3$)C(O$_2$)alkyl, —N(R$^3$)C(O$_2$)alkenyl, —N(R$^3$)C(O$_2$)alkynyl, —N(R$^3$)C(O$_2$)(alkyl)oxy(alkyl), —N(R$^3$)C(O$_2$)(alkyl)thio(alkyl), —OC(O$_2$)alkyl, —OC(O$_2$)alkenyl, —OC(O$_2$)alkynyl, —OC(O$_2$)(alkyl)oxy(alkyl), —OC(O$_2$)(alkyl)thio(alkyl), —N(R$^3$)C(S)alkyl, —N(R$^3$)C(S)alkenyl, —N(R$^3$)C(S)alkynyl, —N(R$^3$)C(S)(alkyl)oxy(alkyl), —N(R$^3$)C(S)(alkyl)thio(alkyl), —N(R$^3$)C(S)N(alkyl), —N(R$^3$)C(S)N(alkenyl), —N(R$^3$)C(S)N(alkynyl), —N(R$^3$)C(S)N(alkyl)oxy(alkyl), —N(R$^3$)C(S)N(alkyl)thio(alkyl), —N(R$^3$)C(S)S(alkyl), —N(R$^3$)C(S)S(alkenyl), —N(R$^3$)C(S)S(alkynyl), —N(R$^3$)C(S)S(alkyl)oxy(alkyl), —N(R$^3$)C(S)S(alkyl)thio(alkyl), —SC(S)S(alkyl), —SC(S)S(alkenyl), —SC(S)S(alkynyl), —SC(S)S(alkyl)oxy(alkyl), and —SC(S)S(alkyl)thio(alkyl);

M is hydrogen, a pharmaceutically acceptable cation, or a metabolically cleavable leaving group;

Y is independently selected from the group consisting of hydrogen, R$^{1-6}$, R$^8$, R$^{10}$, —OR$^3$, —OR$^{11}$, —OR$^{12}$, R$^3$S—, R$^5$S—, R$^3$SO—, R$^5$SO—, R$^3$SO$_2$—, R$^5$SO$_2$—, CF$_3$O—, CF$_3$S—, CF$_3$SO—, —CF$_3$SO$_2$, —OCH$_2$oxycyclopropyl, —OCH$_2$C(O)OR$^3$, —OCH$_2$OR$^3$, —OCH$_2$C(O)R$^3$, —OCH$_2$C$_{3-8}$cycloalkyl, —OCH$_2$CH(R)R$^3$, —OCH$_2$cyclopropyl, —OCH$_2$aryl, —OCH$_2$CH(OH)CH$_2$OH, aryl-CH$_2$SO$_2$—, (R$^3$)$_2$CHCH$_2$SO$_2$—, —CH$_2$CH(OH)CH$_2$OH, CF$_3$SO$_2$—, R$^3$R$^4$N—, —OCH$_2$CO$_2$R$^3$, —NR$^3$COR$^3$, —OCONH$_2$, —OCONR$^3$R$^4$, —CONH$_2$, —CONR$^3$R$^4$, —CR$^3$R$^3$R$^4$, —SO$_2$NR$^3$R$^4$, —SONR$^3$R$^4$, CH$_3$OCH$_2$ONR$^3$R$^6$, —SNR$^3$R$^4$, —CO$_2$R$^3$, —NR$^3$R$^4$SO$_2$R$^3$, —NR$^3$R$^4$SOR, —COR$^3$, —CONR$^3$, —NO$_2$, —CN, —N(R$^5$)CONR$^3$R$^4$, —CH$_2$N(R$^5$)CONR$^3$R$^4$, —R$^6$NR$^3$R$^4$, —OR$^6$NR$^3$R$^4$, —O(O)CR$^5$, —O(O)CNR$^3$R$^4$, —OR$^6$

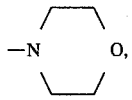

—SR$^6$NR$^3$R$^4$, —S(O)R$^6$NR$^3$R$^4$, —SO$_2$R$^6$NR$^3$R$^4$,

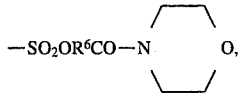

—SR$^6$OH, —S(O)R$^6$OH, —SO$_2$R$^6$OH, —OR$^6$OC(O)N(CO$_2$R$^6$)R$^6$, a heterocycle selected from the group consisting of pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbozolyl, benzamidazolyl, and isoxazolyl; wherein the heterocycle is optionally substituted with a group selected from R$^{1-6}$, R$^8$, R$^{10}$, —OR$^3$, —OR$^{11}$, —OR$^{12}$, R$^3$S—, R$^5$S—, R$^3$SO—, R$^5$SO—, R$^3$SO$_2$—, R$^5$SO$_2$—, CF$_3$O—, CF$_3$S—, CF$_3$SO—, —CF$_3$SO$_2$, —OCH$_2$oxycyclopropyl, —OCH$_2$C(O)OR$^3$, —OCH$_2$OR$^3$, —OCH$_2$C(O)R$^3$, —OCH$_2$C$_{3-8}$cycloalkyl, —OCH$_2$CH(R)R$^3$, —OCH$_2$cyclopropyl, —OCH$_2$-aryl, —OCH$_2$CH(OH)CH$_2$OH, aryl-CH$_2$SO$_2$—, (R$^3$)$_2$CHCH$_2$SO$_2$—, —CH$_2$CH(OH)CH$_2$OH, CF$_3$SO$_2$—, R$^3$R$^4$N—, —OCH$_2$CO$_2$R$^3$, —NR$^3$COR$^3$, —OCONH$_2$, —OCONR$^3$R$^4$, —CONH$_2$, —CONR$^3$R$^4$, —CR$^3$R$^3$R$^4$, —SO$_2$NR$^3$R$^4$, —SONR$^3$R$^4$, CH$_3$OCH$_2$ONR$^3$R$^6$, —SNR$^3$R$^4$, —CO$_2$R$^3$, —NR$^3$R$^4$SO$_2$R$^3$, —NR$^3$R$^4$SOR, —COR$^3$, —CONR$^3$, —NO$_2$, —CN, —N(R$^5$)CONR$^3$R$^4$, —CH$_2$N(R$^5$)CONR$^3$R$^4$, —R$^6$NR$^3$R$^4$, —OR$^6$NR$^3$R$^4$, —O(O)CR$^5$, —O(O)CNR$^3$R$^4$, —OR$^6$, —SR$^6$NR$^3$R$^4$, —S(O)R$^6$NR$^3$R$^4$, —SO$_2$R$^6$NR$^3$R$^4$, —SO$_2$OR$^6$CO, —SR$^6$OH, —S(O)R$^6$OH, —SO$_2$R$^6$OH, and —OR$^6$OC(O)N(CO$_2$R$^6$)R$^6$,

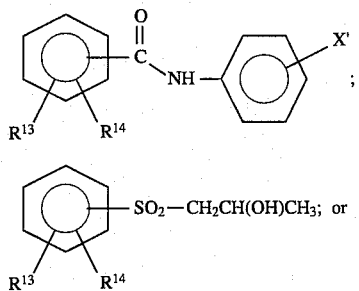

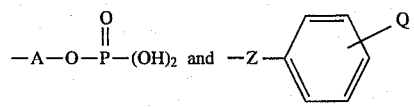

wherein X' is selected from the group consisting of halo, —C(O)aryl, $CF_3$, —$OR^3$, —$CH_2OR^3$, —$CH_2CO_2R^3$, —$CH_2COR^3$, —$NHCH_2COOR^3$, —$N^+ R^3R^3R^4R^7$, $R^1$ is selected from the group consisting of hydrogen, halogen, lower alkyl, halo lower alkyl, —COOH, —$CONR^{16}R^{17}$, —$COOR^3$, alkenyl, —$COR^3$, —$CH_2OR^3$, lower alkynyl, —$CH_2NR^4R^3$, —$CH_2SR^3$, =O, —$OR^3$, and —$NR^3R^4$;

$R^2$ is selected from the group consisting of

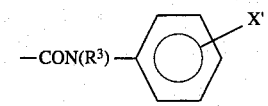

$R^3$ and $R^4$ are independently selected from the group consisting of cyclic and acyclic alkyl, alkenyl, alkynyl, aryl, aralkyl, alkaryl, hydrogen, $C_{1-6}$ alkoxy-$C_{1-10}$ alkyl, $C_{1-6}$ alkylthio-$C_{1-10}$ alkyl, and $C_{1-10}$ substituted alkyl, wherein the substituent is independently selected from hydroxy and carbonyl and is located on any of $C_{1-10}$;

$R^5$ is selected from the group consisting of cyclic and acyclic lower alkyl, lower alkenyl, lower alkynyl, halo lower alkyl, halo lower alkenyl, halo lower alkynyl, aralkyl, and aryl;

$R^6$ is selected from the group consisting of cyclic or acyclic lower alkyl, lower alkenyl, lower alkynyl, aralkyl, halo lower alkyl, halo lower alkenyl, halo lower alkynyl, and aryl;

$R^7$ is an organic or inorganic anion;

$R^8$ is selected from the group consisting of halo alkyl, halo lower alkyl, halo lower alkenyl, halo lower alkynyl, lower alkenyl, lower alkynyl, aralkyl, and aryl;

$R^9$ is independently selected from the group consisting of hydrogen, halogen, lower alkyl, halo lower alkyl, lower alkenyl, lower alkynyl, —$CONR^3R^4$, —$COR^5$, —$CO_2R^5$, —$CH_2$ $OR^5$, —$CH_2NR^5R^5$, —$CH_2SR^5$, =O, =$NR^5$, —$NR^3R^4$, —$NR^3R^4$§$R^7$, and —$OR^5$;

$R^{10}$ is selected from the group consisting of —$R^3$, —$R^8$, —$C(O)N(OR^3)R^3$, and —$OR^3$;

$R^{11}$ is selected from the group consisting of $C_1$ to $C_{12}$ alkyl; substituted $C_1$ to $C_{12}$ alkyl, wherein the substituent is selected from the group consisting of hydroxy and amino; alkenyl, lower alkoxy-alkyl, alkylcarbonylalkyl, -alkylamino, -alkylamino(alkyl or dialkyl), lower alkyl-S(O)$_m$-lower alkyl in which m is 0, 1 or 2, imidazolyl lower alkyl, morpholinyl lower alkyl, thiazolinyl lower alkyl, piperidinyl lower alkyl, imidazolylcarbonyl, morpholinyl carbonyl, amorpholinyl-(lower alkyl)aminocarbonyl, N-pyrrylpyridinyl-lower alkyl, pyridylthio-lower alkyl, morpholinyl-lower alkyl, hydroxyphenylthio-lower alkyl, cyanophe-nylthio-lower alkyl, imidazolylthio-lower alkyl, triazolylthio-lower alkyl, triazolylphenylthio-lower alkyl, tetrazolylthio-lower alkyl, tetrazolylphenylthio-lower alkyl, aminophenylthio-lower alkyl, N,N-disubstituted aminophenylthio-lower alkyl, wherein the substituents each independently represent lower alkyl; amidinophenylthio-lower alkyl, phenylsulfinyl-lower alkyl, or phenylsulfonyl lower alkyl, $R^{12}$ is selected from the group consisting of alkyl, substituted alkyl, wherein the substituent is selected from the group consisting of hydroxy and amino; -lower alkyl-O—$R^{18}$, —$C(O)(CH_2)_2 CO_2^- M^+$, or —$SO_3^- M^+$, wherein M is a pharmaceutically acceptable cation; -lower alkylcarbonyl-lower alkyl, -carboxy lower alkyl, -lower alkylamino-lower alkyl, N,N-disubstituted amino lower alkyl-, wherein the substituents are independently selected from lower alkyl; pyridyl-lower alkyl, imidazolyl-lower alkyl, imidazolyl-X"-lower alkyl wherein X" is selected from thio and amino, morpholinyl-lower alkyl, pyrrolidinyl-lower alkyl, thiazolinyl-lower alkyl, piperidinyl-lower alkyl, morpholinyl-lower hydroxyalkyl, N-pyrryl, piperazinyl-lower alkyl, N-substituted piperazinyl-lower alkyl, wherein the substituent is lower alkyl, triazolyl-lower alkyl, tetrazolyl-lower alkyl, tetrazolylamino-lower alkyl, and thiazolyl-lower alkyl, $R^{13}$, $R^{14}$ and $R^{15}$ are independently selected from the group consisting of BO— wherein B is —$CH_2$-oxacyclopropyl, —$CH_2OR^3$, —$CH_2C(O)R^3$, —$CH_2CH(R^3)R^3$, —$CH_2$Aryl, —$CH_2CH(OH)$—$CH_2OH$; $R^3C(R^3)_2CH_2SO_2$; or $R^{13}$—$R^{14}$ or $R^{14}$—$R^{15}$ are joined together to form a bridge such as —$OCHR^2CHR^2$—$S(O)_n$— wherein n is 0 to 3; or —CON($R^3$)—⟨phenyl⟩—X'

$R^{16}$ and $R^{17}$ are each independently selected from the group consisting of $C_{1-6}$ alkyl and hydrogen;

$R^{18}$ is selected from the group consisting of —$PO_2(OH)^- M^+$ and —$PO_3(M^+)_2$, wherein $M^+$ is a pharmaceutically acceptable cation, $R^{19}$ is selected from the group consisting of H, lower alkyl, and lower alkenyl; and $R^{20}$ is H, halogen, lower alkoxy, or lower alkyl.

2. A compound of formula

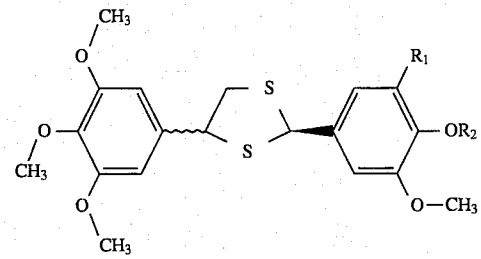

wherein $R^1$ is selected from the group consisting of $NHCONOHCH_3$, $NHCSNOHCH_3$, $NHCONOHC_4H_9$, $NHCONOHC(CH_3)_3$, $CH_2N(OH)C(O)NH_2$, $CH_2N(OH)C(O)CH_3$, $NO_2$, $NH_2$, $NHCONOHC_6H_4Cl$, $N(CH_3)_2$, $NHCONOM^1CH_3$, and $NHCONOM^2CH_3$;

$R^2$ is selected from $CH_3$, $CH_2CH$=$CH_2$, $CH_2CH_2SC_6H_4OH$, $CH_2CH_2$ $SC_6H_4CN_6$ and CH₂CH₂SC₆H₄Br;

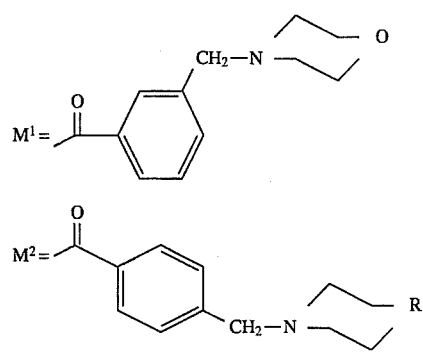

and R is CH₂.

3. A compound according to claim 2, wherein R¹ is NHCONOHCH₃ and R² is CH₂CH₂SC₆H₄CN.

4. The compound of claim 1 wherein Ar¹ and Ar² are independently selected from the group consisting of

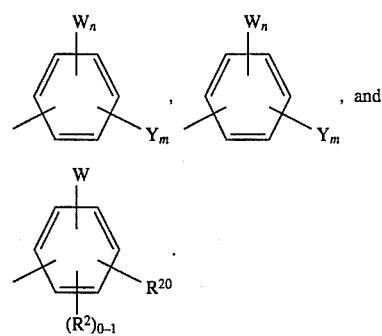

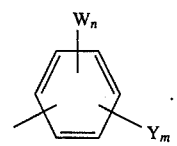

5. The compound of claim 1 wherein at least one of Ar¹ and Ar² is:

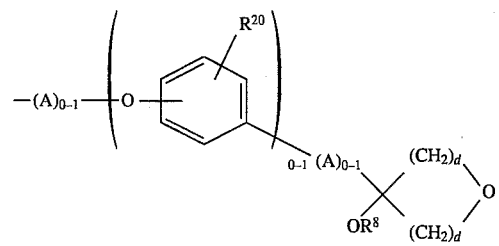

6. The compound of claim 1 wherein W is —AN(OM)C(O)N(R³)R⁴.

7. The compound of claim 1 wherein W is —AN(R³)C(O)N(OM)R⁴.

8. The compound of claim 1 wherein W is —N(OM)C(O)N(R³)R⁴.

9. The compound of claim 1 wherein W is —N(R³)C(O)N(OM)R⁴.

10. The compound of claim 1 wherein A is selected from the group consisting of alkyl, alkenyl, and alkynyl.

11. The compound of claim 1 wherein A is selected from the group consisting of alkaryl and aralkyl.

12. The compound of claim 1 wherein Y is selected from the group consisting of —OR³, —OR¹¹, and —OR¹².

13. The compound of claim 1 wherein Y is selected from the group consisting of R³S—, R⁵S—, R³SO—, R⁵SO—, R³SO₂—, and R⁵SO₂—.

14. The compound of claim 1 wherein Y is selected from the group consisting of CF₃O—, CF₃S—, CF₃SO—, and —CF₃SO₂.

15. The compound of claim 1 wherein W is —R⁴N(R³)C(O)N(OM)A.

16. The compound of claim 15 wherein R⁴ is methyl.

17. The compound of claim 1 wherein W is an oxalkane of the structure:

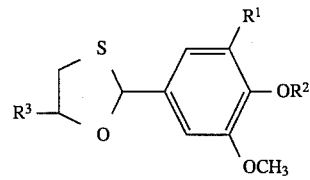

wherein n and m are independently 1–4.

18. The compound of claim 17 wherein n and m are 2 and R¹⁹ is methyl.

19. The compound of claim 1 wherein M is hydrogen.

20. The compound of claim 19 wherein R³ is methyl.

21. The compound of claim 1 wherein Y is R³SO₂—, R⁵SO₂— or —OCH₂-aryl.

22. The compound of claim 1 wherein R¹ and R² are hydrogen.

23. The compound of claim 1 wherein R¹¹ is C₁ to C₁₂ substituted alkyl, wherein the substituent is hydroxy or amino.

24. The compound of claim 1 wherein R¹¹ is hydroxyphenylthio-lower alkyl or cyanophenylthio-lower alkyl.

25. The compound of claim 1 wherein R¹¹ is imidazolylthio-lower alkyl or triazolylthio-lower alkyl.

26. The compound of claim 1 wherein R¹¹ is triazolylphenylthio-lower alkyl or tetrazolylphenylthio-lower alkyl.

27. The compound of claim 1 wherein R¹¹ is aminophenylthio-lower alkyl or N,N-disubstituted aminophenylthio-lower alkyl.

28. The compound of claim 1 wherein X is selected from the group consisting of O and S, W is selected from the group consisting of —AN(R³)C(O)N(OM)R⁴, —AN(OM)C(O)N(R³)R⁴ and —AN(R³)C(O)N(OM)R⁴, A is selected from the group consisting of alkyl, alkenyl, alkynyl, alkaryl and aralkyl, M is hydrogen, Y is selected from the group consisting of —OR³, —OR¹¹, —OR¹², R³SO₂—, and —OCH₂-aryl, and R¹ and R² are hydrogen.

29. A compound of formula

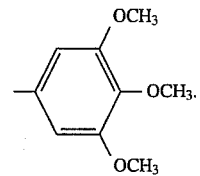

wherein R¹ is selected from the group consisting of NHC(O)N(OH)C(CH₃)₃ and N(CH₃)₂; R² is CH₂CH=CH₂ and R³ is

* * * * *